US009228168B2

(12) United States Patent
Morris et al.

(10) Patent No.: US 9,228,168 B2
(45) Date of Patent: *Jan. 5, 2016

(54) FEED MEDIA

(75) Inventors: Arvia Eleanor Morris, Seattle, WA (US); Aurora Villegas Viaje, Lake Forest Park, WA (US); Erika Pineda, Queretaro (MX)

(73) Assignee: Amgen Inc., Thousand Oaks, CA (US)

( * ) Notice: Subject to any disclaimer, the term of this patent is extended or adjusted under 35 U.S.C. 154(b) by 1052 days.

This patent is subject to a terminal disclaimer.

(21) Appl. No.: 13/245,600

(22) Filed: Sep. 26, 2011

(65) Prior Publication Data

US 2012/0021459 A1 Jan. 26, 2012

Related U.S. Application Data

(63) Continuation of application No. 12/118,459, filed on May 9, 2008, now Pat. No. 8,053,236.

(60) Provisional application No. 60/917,569, filed on May 11, 2007.

(51) Int. Cl.
*C12N 5/00* (2006.01)

(52) U.S. Cl.
CPC .............. *C12N 5/0037* (2013.01); *C12N 5/005* (2013.01); *C12N 2500/32* (2013.01); *C12N 2500/34* (2013.01); *C12N 2510/02* (2013.01)

(58) Field of Classification Search
CPC .... C12N 1/00; C12N 5/0018; C12N 2500/32; C12N 2500/99; C12N 5/0037; C12N 2500/34; C12N 2510/02; C12N 5/005
USPC ........................................ 435/358, 70.9, 404
See application file for complete search history.

(56) References Cited

U.S. PATENT DOCUMENTS

| 5,474,931 | A | 12/1995 | DiSorbo et al. |
| 5,672,502 | A | 9/1997 | Birch et al. |
| 6,180,401 | B1 | 1/2001 | Chen et al. |
| 6,900,056 | B2 | 5/2005 | Lee et al. |
| 6,949,382 | B2 | 9/2005 | Crawford |
| 2005/0069979 | A1 | 3/2005 | Zeng et al. |
| 2005/0101011 | A1 | 5/2005 | Tsao |
| 2006/0292692 | A1 | 12/2006 | Xu |
| 2008/0254513 | A1 | 10/2008 | Cayli |

FOREIGN PATENT DOCUMENTS

| EP | 2 152 856 B1 | 2/2010 |
| WO | 03/106661 A2 | 12/2003 |
| WO | 03/106661 A3 | 12/2003 |
| WO | 2005/035748 A1 | 4/2005 |
| WO | 2006/050050 A2 | 5/2006 |

OTHER PUBLICATIONS

Supplementary European Search Report, dated Apr. 9, 2010.

ATCC Cell Biology Catalog 2007, Section IV: Technical Information, "Complete Growth Media," pp. 267-271.
ATCC Reagents and Kits Product Catalog No. 30-2002, "Dulbecco's Modified Eagle's Medium (DMEM) Formulation."
ATCC Reagents and Kits Product Catalog No. 30-2003, "Eagle's Minimum Essential Medium (DMEM) Formulation."
ATCC Reagents and Kits Product Catalog No. 30-2004, "F-12K Medium Formulation."
ATCC Reagents and Kits Product Catalog No. 30-2005, "Iscove's Modified Dulbecco's Medium (IMDM) Formulation."
ATCC Reagents and Kits Product Catalog No. 30-2006, "DMEM: F-12 Medium Formulation."
ATCC Reagents and Kits Product Catalog No. 30-2007, "McCoy's 5A Medium Formulation."
ATCC Reagents and Kits Product Catalog No. 30-2008, "Leibovitz's L-15 Medium Formulation."
ATCC Reagents and Kits Product Catalog No. 46-X, "Hybri-Care Medium Formulation."
Invitrogen™ Technical Resources—Media Formulation, "F-10 Nutrient Mixture (Ham) (1X) liquid," catalog No. 12390035.
Bibila TA et al., "Monoclonal antibody process development using medium concentrates," Biotechnol Prog 10:87-96, 1994.
Sauer PW et al., "A high-yielding, generic fed-batch cell culture process for production of recombinant antibodies," Biotechnol Bioeng 67:585-597, 2000.
Simon and Rajewsky, "Antibody domain mutants demonstrate autonomy of the antigen binding site," EMBO J 9(4):1051-1056, 1990.
Zhou W et al., Alteration of mammalian cell metabolism by dynamic nutrient feeding,' Cytotechnology 24:99-108, 1997.
Nishiuch et al., "Cytotoxicity of Cysteine in Culture Media," In Vitro 12(9):635-638, 1976.
Product Information Insert, Pyruvate, Lonza, 2007.
Product Information Insert, Eagle's MEM "Nissui", 2010.
Appendix 1—Merck Experimental data submitted by the Opponent with the Grounds of Opposition, filed May 29, 2013.
1st Declaration and CV of Dr. Arvia E. Morris, 2013.
Stedman's Medical Dictionary, 26th Ed., Ed.: Spraycar and Randolph, Williams & Wilkens, p. 1418, 1995.
The Merck Index, 14th Ed., O'Neil et al., eds., Merck & Co., Inc., pp. 467-468 and 1690-1691, 2006, submitted with Proprietor's Response to Notice of Opposition in EP 2 152 856.
Waymouth, "Preparation and use of Serum-Free Culture Media," in Cell Culture Methods for Molecular and Cell Biology, vol. 1, pp. 23-68, pp. 44-45, Alan R. Liss, Inc., New York, 1984.
Healy et al., "Nutrition of Animal Cells in Tissue Culture," Can. J. Biochem. Physiol. 32:327-337, 1954.

(Continued)

*Primary Examiner* — Taeyoon Kim
(74) *Attorney, Agent, or Firm* — Alex A. Andalis (57) ABSTRACT

The invention provides stable feed media containing pyruvate and methods for stabilizing feed media by adding pyruvate. The invention further provides methods for producing proteins using such media and proteins produced through the use of such methods.

34 Claims, 3 Drawing Sheets

(56) References Cited

OTHER PUBLICATIONS

Freshney, Culture of Animal Cells: A Manual of Basic Technique, Fifth Ed., John Wiley & Sons, Inc., Hoboken, New Jersey, pp. 161-162, 2005.

Sigma Catalog, "Products for Life Science Research," pp. 345-490, 2000-2001.

Summary Table, "Media and Nutrient Recipes," in Sigma Products for Life Science Research catalog, 2000-2001.

Jocelyn PC, Biochemistry of the SH Group, Academic Press, Chapter 3, pp. 63-93, 1972.

Appendix 2 to Proprietor's Response to Notice of Opposition, filed Dec. 20, 2013.

Cysteine/pyruvate: supplementary experiments of Dr. Aline Zimmer, Jul. 15, 2014.

Declaration of Martin Jordan, dated Jul. 29, 2014.

Oxford Advanced Learner's Dictionary, AS Hornby, Oxford University Press, Entry "precipitate" and "sediment," 1989.

Second Declaration of Dr. Arvia Morris, dated Sep. 26, 2014.

The Merck Index, 12$^{th}$ Ed., Budavari et al., eds., Merck & Co., Inc., p. 471, 1996.

Excerpt from "Design and Analysis of Experiments," 6$^{th}$ Ed., DC Montgomery, John Wiley & Sons, eds., pp. 8-9, 2005.

Excerpts from the "JMP® User's Guide, Version 4," pp. 53-54 and JMP® Statistics and Graphics Guide, JMP Version 4, pp. 297-314, 2000.

Deshpande et al., "Microplates with integrated oxygen sensing for medium optimization in animal cell culture," Cytotechnology 46:1-8, 2004.

Mohamed et al., "Optimization of Composition of Media for the Production of Extracellular Glucoamylase by *Candida guilliermendii*," Pak. J. Biol. Sci. 10(19):3322-3329, 2007.

Nagarjun et al., "Optimization of Lactic Acid Production in SSF by *Lactobacillus amylovorus* NRRL B-4542 Using Taguchi Methodology," J. Microbiol. 43(1):38-43, 2005.

Sandadi et al., "Application of Fractional Factorial Designs to Screen Active Factors for Antibody Production by Chinese Hamster Ovary Cells," Biotechnol. Prog. 22:595-600, 2006.

Mueller et al., "Improved fed-batch bioprocesses using chemically modified amino acids in concentrated feeds," BMC Proceedings 7(Suppl 6):P46, 2013.

Zimmer et al., "Improvement and simplification of fed-batch bioprocesses with a highly soluble phosphotyrosine sodium salt," J. Biotechnol. 186:110-118, 2014.

Freshney, Culture of Animal Cells—A Manual of Basic Techniques, Wiley-Liss, Inc., New York, pp. 114-119, 1994.

Römpp Chemie Lexikon, Entry "Nephelometrie," section "Use" ("Verwendung") 2008.

Product information sheet on the Thermo Scientific HyClone Cell Boost 1 (R05.2), 2010.

Printout from the online version of Stedman's Medical Dictionary, 28$^{th}$ Ed., Lippincott, Williams & Wilkins, eds., Philadelphia USA, "precipitate" and precipitation' entries, 2006.

Becton, Dickinson and Company, "Difco™ & BBL™ Manual: Manual of Microbiological Culture Media," Zimbro MJ and Power DA, Eds., pp. iii, v, vii, viii, ix, x, 3-17, 22-24, 33, 34, 37, 38, 52-58, 131-133, 155, 156, 170-173, 178-180, 190-192, 534, 543, 544, 547, 548, 551-560, 2003.

MacDonaill, "Calcium Precipitation from Mammalian Physiological Salines (Ringer Solutions) and the Preparation of High [Ca] Media,"J. Pharmacological Methods 14:147-155, 1985.

Taub M, "Growth of Primary and Established Kidney Cell Cultures in Serum-Free Media," Chapter 1, in Methods for Serum-Free Culture of Epithelial and Fibroblastic Cells, Barnes DW, et al., Eds., Alan R. Liss, Inc., New York, pp. 3-24, 1984.

Leffert HL, et al., "Primary Culture of Hepatocytes," Chapter 4, in Methods for Serum-Free Culture of Epithelial and Fibroblastic Cells, Barnes DW, et al., Eds., Alan R. Liss, Inc., New York, pp. 43-55, 1984.

AU Office Action, Application No. 2008251405, dated Apr. 19, 2011.
CA Office Action, Application No. 2,687,082, dated Nov. 4, 2011.
Office Action, U.S. Appl. No. 12/118,459, mailed Nov. 26, 2010.
International Search Report, mailed Aug. 4, 2008.
EP Notice of Opposition, dated May 29, 2013.
Notice of Opposition (German), dated May 29, 2013.
EPO Form 2310, Opposition Division Preliminary Opinion, dated Feb. 24, 2014.
Opponent's Last Submission (English), dated Aug. 5, 2014.
Opponent's Last Submission, dated Aug. 7, 2014.

FEED MEDIA

CROSS REFERENCE TO RELATED APPLICATIONS

This application is a continuation of U.S. application Ser. No. 12/118,459, filed May 9, 2008, now allowed, which claims the benefit of U.S. Provisional Application No. 60/917,569, filed May 11, 2007, the disclosure of each of which is incorporated herein by reference in its entirety.

FIELD OF THE INVENTION

The invention is in the field of cell culture media and methods.

BACKGROUND OF THE INVENTION

Large-scale fed-batch culture of mammalian cells, especially Chinese Hamster Ovary (CHO) cells, is widely used to produce proteins used in a variety of applications, such as diagnostic, therapeutic, and research uses. Particular attention has focused on CHO cells because they have been extensively characterized and have been approved for use in clinical manufacturing by regulatory agencies. Such cultures are typically maintained for days, or even weeks, while the cells produce the desired protein(s). During this time the culture can be supplemented with a feed medium containing components, such as nutrients and amino acids, which are consumed during the course of the culture. Such feeding has been shown to improve protein production by a mammalian cell culture. See e.g., U.S. Pat. No. 5,672,502. Even incremental improvements in protein production can be valuable, given the expense and difficulty of building and obtaining regulatory approval for large-scale, commercial culture facilities.

Concentrated feed media are often used in fed batch culture processes to improve protein titer, cell growth, and/or cell viability. Some components present at high concentration in feed media may precipitate during storage, especially when the pH of the medium is near neutrality. Precipitation of medium components during storage prior to use of a medium is very undesirable because it adds an element of uncertainty. When medium components precipitate, the concentration of medium components in solution, versus in the precipitate, will be unknown. Since concentrations of various medium components can affect the quantity and quality of a protein produced by a culture, this is an element of uncertainty that is highly undesirable in a commercial culture process, in which culture conditions are, optimally, carefully controlled. Moreover, commercial processes may be subjected to stringent regulatory review. Thus, feed media with high concentrations of amino acids that can be stored for a period of time without precipitating would provide significant advantages.

SUMMARY OF THE INVENTION

The invention provides stable feed media containing pyruvate, methods for stabilizing feed media comprising adding pyruvate to a medium, methods for using stable feed media, and proteins produced by cultures fed with a medium of the invention.

In one embodiment, the invention encompasses a method for stabilizing a concentrated feed medium to be used for feeding a mammalian cell culture comprising adding to the feed medium at least about 9, 18, 25, 30, 35, 40, 45, or 50 mM pyruvate, wherein the feed medium can comprise cysteine and/or cystine, wherein the sum of the concentrations of cysteine and/or cystine can be at least about 7.9 mM, wherein the pH of the feed medium can be from about 5.8 to about 7.4, wherein the feed medium can comprise tyrosine at a concentration of not more than about 4.4 mM or 4.6 mM tyrosine, and wherein the medium can be stable for at least about 1, 2, or 3 weeks at room temperature. The pyruvate can be sodium pyruvate. The pH of the feed medium can be from about 6.0 to about 7.2 and/or at least about 6.3, 6.4, 6.5, 6.6, 6.7, or 6.8 and not more than about 7.4. The feed medium can comprise at least about 5.0, 6.0, 7.0, 12.0, 21.0, 35.0, 40.0 or 45.0 mM cysteine and/or at least about 0.5, 1.0, 1.5, 2.0, or 4.0 mM cystine. The feed medium may comprise from about 7 mM to about 16 mM cysteine or from about 7.5 mM to about 13 mM cysteine. The feed medium can comprise tyrosine at a concentration of at least about 2, 3, or 4 mM tyrosine. The feed medium can comprise a protein hydrolysate and may be serum free. The osmolarity of the feed medium can be from about 200 mOsm to about 1300 mOsm, from about 250 mOsm to about 1000 mOsm, from about 200 mOsm to about 500 mOsm, from about 500 mOsm to about 1000 mOsm, from about 700 mOsm to about 900 mOsm, from about 270 mOsm to about 900 mOsm, from about 300 mOsm to about 830 mOsm, or from about 200 mOsm to about 400 mOsm. The mammalian cell culture can contain CHO cells.

In another embodiment, the invention provides a method for stabilizing a feed medium comprising adding about 30 to 40 mM pyruvate to a feed medium which can comprise (a) from about 3 mM and to about 4.0 mM tyrosine, and (b) cysteine and/or cystine, wherein the sum of the concentrations of cysteine and/or cystine is at least about 7.9 mM, and wherein the pH of the feed medium is from about 5.8 to about 7.4. The pH may be from about 6.0 mM to about 7.4 mM and/or at least about 6.3, 6.4, 6.5, 6.6, 6.7, or 6.8 and not more than about 7.4. The feed medium can be stable for at least about 1, 2, 3, or 4 weeks at room temperature or at 4-8° C.

In a further embodiment, the invention comprises a feed medium for a mammalian cell culture that can comprise at least about 9, 18, 25, 30, 35, 40, 45, or 50 mM pyruvate and at least about 5 mM cysteine, wherein the pH of the feed medium can be from about 5.8 to about 7.4, wherein the feed medium can comprise tyrosine at a concentration of not more than about 4.4 mM, and wherein the medium can be stable for at least about 1, 2, or 3 weeks at room temperature or at 4-8° C. The pyruvate can be sodium pyruvate. The pH of the feed medium can be from about 6.0 to about 7.2 and/or at least about 6.3, 6.4, 6.5, 6.6, 6.7, or 6.8 and not more than about 7.4. The feed medium can also comprise at least about 6, 7, 12, 21, 35, 40, or 45 mM cysteine and/or at least about 0.5, 1.0, 1.5, 2.0, or 4.0 mM cystine. The feed medium can comprise tyrosine, optionally at a concentration of at least about 2, 3, 4, or 4.2 mM tyrosine. The feed medium can comprise a protein hydrolysate and may be serum free. The osmolarity of the feed medium can be from about 200 mOsm to about 1300 mOsm, from about 250 mOsm to about 1000 mOsm, from about 200 mOsm to about 500 mOsm, from about 500 mOsm to about 1000 mOsm, from about 700 mOsm to about 900 mOsm, from about 270 mOsm to about 900 mOsm, from about 300 mOsm to about 830 mOsm, or from about 200 mOsm to about 400 mOsm. The mammalian cell culture can be a Chinese Hamster Ovary (CHO) cell culture.

In a further embodiment, the invention encompasses a feed medium for a CHO cell culture, which can comprise (1) from about 3 mM and to about 4.0 mM tyrosine, (2) cysteine and/or cystine, wherein the sum of the concentrations of cysteine and/or cystine is at least about 7.9 mM, and (3) about 30 to 40 mM pyruvate, wherein the pH of the feed medium can be from about 5.8 to about 7.4 or from about 6.0 to about 7.4. The feed medium can be stable for at least about 1, 2, 3, or 4 weeks at room temperature or a 4-8° C.

In other embodiments, the invention provides various methods of utilizing the feed media of the invention. For example, the invention provides a method for culturing cells comprising culturing the cells in a base medium and feeding the culture with a feed medium of the invention. Further, the invention encompasses a method for producing a protein comprising culturing mammalian cells that produce the protein in a base medium, feeding the culture with a feed medium of the invention, and recovering the protein from the culture medium. The protein may be a recombinant protein and can be purified. The base medium used in the culture may be serum free, and the cells may be cultured in at least one growth phase and at least one production phase. In still another aspect, the invention provides a method for increasing production of a protein produced by cultured mammalian cells, which may be CHO cells, comprising feeding the cultured cells with a feed medium of the invention. Feeding may occur one or more times during the culture and may be adjusted so as to keep certain culture components within certain concentration ranges.

In a further aspect, the invention encompasses a protein produced by any of the methods of the invention.

BRIEF DESCRIPTION OF THE FIGURES

FIG. 2A: This figure was created using the day 21 data described in Example 4 and Table 5 and using JMP® software (SAS Institute Inc., Cary, N.C.). The upper row of five boxes show the likelihood of having no precipitate "P(day 21=0)," and the lower row of five boxes show the likelihood of having a precipitate "P(day 21=1)" at day 21. On the vertical y axes, 1.00 means 100% probability, and 0.00 means zero probability. The dotted vertical lines in each box indicate the concentration at which the medium component or storage temperature listed below each vertical column of two boxes is set in all other columns of boxes. In the column of two boxes directly over the labeled component or temperature, the concentration of the component or the temperature is varied in the range shown along the x axis below each vertical column of two boxes. The concentrations listed along the x axis are expressed in millimolar units, and the temperatures are expressed as degrees centigrade. For example sodium pyruvate is set at 34.65 mM in all boxes other than the two directly above the words "sodium pyruvate." In these two boxes, sodium pyruvate varies from about 5 mM to almost 35 mM.

FIG. 3A: This figure was made using the day 21 data described in Example 5 and Table 6 using JMP® software (SAS Institute Inc., Cary, N.C.). It is similar to FIG. 2A, although the exact concentrations at which the various medium components are set (marked directly over the name of the medium component) differs somewhat. Sodium pyruvate is set at 35.11 mM in all columns other than the rightmost column, in which the sodium pyruvate concentration varies.

DETAILED DESCRIPTION OF THE INVENTION

The instant invention provides concentrated feed media for use in fed batch culture of eukaryotic, optionally mammalian, cells that can be soluble at room temperature and can be stored for a reasonable time without precipitation. For use in mammalian cell culture, a feed medium can have a pH such that, when added to the culture, it will not bring the culture outside of a physiologic range, for example, from about pH 6.5 to about 7.5. These stable, concentrated feed media can contain high concentrations of amino acids such as cysteine and/or cystine and/or tyrosine and high concentrations of pyruvate. The invention thus contributes to more operationally advantageous and robust cell culture processes. The feed media of the invention are particularly useful for large scale, commercial cultures of mammalian cells that produce a recombinant protein, which can be used as, for example, a therapeutic, a diagnostic, or a research reagent. The feed medium of the invention may be stored at room temperature or at refrigerator temperature.

The term "stable," as used herein, refers to a medium that does not precipitate upon storage for at least a specified period of time, such as at least about 1 week, 2 weeks, 3 weeks, or 4 weeks. The medium may be stored, for example, at room temperature (which is 15-30° C., as meant herein) or at refrigerator temperature (which is 4-8° C., as meant herein). Similarly, when a medium is said to be "stabilized" for some period of time, it means that solutes in the media do not form a precipitate and come out of solution.

"Pyruvate" includes the free form of pyruvic acid as well as acid salts, including sodium pyruvate and other acid salts.

A "base medium," as meant herein, is a medium used for culturing eukaryotic cells which is, itself, directly used to culture the cells and is not used as an additive to other media, although various components may be added to a base medium. For example, if CHO cells were cultured in DMEM, a well-known, commercially-available medium for mammalian cells, and periodically fed with glucose or other nutrients, DMEM would be considered the base medium.

A "feed medium" is a medium used as a feed in a culture of eukaryotic cells, which may be mammalian cells. A feed medium, like a base medium, is designed with regard to the needs of the particular cells being cultured. Thus, a base medium can be used as a basis for designing a feed medium. As described below in more detail, a feed medium can have higher concentrations of most, but not all, components of a base culture medium. For example, some components, such as, for example, nutrients including amino acids or carbohydrates, may be at about 5×, 6×, 7×, 8×, 9×, 10×, 12×, 14×, 16×, 20×, 30×, 50×, 100×, 200×, 400×, 600×, 800×, or even about 1000× of their normal concentrations in a base medium. Some components, such as salts, maybe kept at about 1× of the base medium concentration, as one would want to keep the feed isotonic with the base medium. Components not normally utilized as nutrients in media would not generally be present at increased concentrations in feed media. Thus, some components are added to keep the feed physiologic, and some are added because they are replenishing nutrients to the culture.

A "recombinant protein" is a protein resulting from the process of genetic engineering. Cells have been "genetically engineered" to express a specific protein when recombinant nucleic acid sequences that allow expression of the protein have been introduced into the cells using methods of "genetic engineering," such as viral infection with a recombinant virus, transfection, transformation, or electroporation. See e.g. Kaufman et al. (1990), Meth. Enzymol. 185: 487-511;

*Current Protocols in Molecular Biology*, Ausubel et al., eds. (Wiley & Sons, New York, 1988, and quarterly updates). The term "genetic engineering" refers to a recombinant DNA or RNA method used to create a host cell that expresses a gene at elevated levels or at lowered levels, or expresses a mutant form of the gene. In other words, the cell has been transfected, transformed or transduced with a recombinant polynucleotide molecule, and thereby altered so as to cause the cell to alter expression of a desired protein. The methods of "genetic engineering" also encompass numerous methods including, but not limited to, amplifying nucleic acids using polymerase chain reaction, assembling recombinant DNA molecules by cloning them in *Escherichia coli*, restriction enzyme digestion of nucleic acids, ligation of nucleic acids, and transfer of bases to the ends of nucleic acids, among numerous other methods that are well-known in the art. See e.g. Sambrook et al., Molecular Cloning: A Laboratory Manual, $2^{nd}$ ed., vol. 1-3, Cold Spring Harbor Laboratory, 1989. Methods and vectors for genetically engineering cells and/or cell lines to express a protein of interest are well known to those skilled in the art. Genetic engineering techniques include but are not limited to expression vectors, targeted homologous recombination and gene activation (see, for example, U.S. Pat. No. 5,272,071 to Chappel) and trans activation by engineered transcription factors (see e.g., Segal et al., 1999, Proc. Natl. Acad. Sci. USA 96(6):2758-63). Optionally, the proteins are expressed under the control of a heterologous control element such as, for example, a promoter that does not in nature direct the production of that protein. For example, the promoter can be a strong viral promoter (e.g., CMV, SV40) that directs the expression of a mammalian protein. The host cell may or may not normally produce the protein. For example, the host cell can be a CHO cell that has been genetically engineered to produce a human protein, meaning that nucleic acid encoding the human protein has been introduced into the CHO cell. Alternatively, the host cell can be a human cell that has been genetically engineered to produce increased levels of a human protein normally present only at very low levels (e.g., by replacing the endogenous promoter with a strong viral promoter).

"Substantially similar" proteins are at least about 90% identical to each other in amino acid sequence and maintain or alter in a desirable manner the biological activity of the unaltered protein. As is known in the art, changes in conserved amino acids are more likely to affect the biological function of a protein. Further, conservative amino acid substitutions at any site in a protein are less likely to cause functional changes than non-conservative substitutions. Conservative amino acid substitutions, unlikely to affect biological activity, include, without limitation, the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and these changes in the reverse. See e.g. Neurath et al., *The Proteins*, Academic Press, New York (1979). In addition exchanges of amino acids among members of the following six groups of amino acids will be considered to be conservative substitutions for the purposes of the invention. The groups are: 1) methionine, alanine, valine, leucine, and isoleucine; 2) cysteine, serine, threonine, asparagine, and glutamine; 3) aspartate and glutamate; 4) histidine, lysine, and arginine; 5) glycine and proline; and 6) tryptophan, tyrosine, and phenylalanine. The percent identity of two amino sequences can be determined using the Genetics Computer Group (GCG; Madison, Wis.) Wisconsin package version 10.0 program, 'GAP' (Devereux et al. (1984), *Nucl. Acids Res.* 12: 387) or other comparable computer programs. The preferred default parameters for the 'GAP' program includes: (1) the weighted amino acid comparison matrix of Gribskov and Burgess (1986), *Nucl. Acids Res.* 14: 6745, as described by Schwartz and Dayhoff, eds., *Atlas of Protein Sequence and Structure*, National Biomedical Research Foundation, pp. 353-358 (1979), or other comparable comparison matrices; (2) a penalty of 8 for each gap and an additional penalty of 2 for each symbol in each gap for amino acid sequences; (3) no penalty for end gaps; and (4) no maximum penalty for long gaps.

Fed batch culture is a widely-practiced culture method for large scale production of proteins from mammalian cells. See e.g. Chu and Robinson (2001), Current Opin. Biotechnol. 12: 180-87. A fed batch culture of mammalian cells is one in which the culture is fed, either continuously or periodically, with a feed medium containing nutrients. Feeding can occur on a predetermined schedule of, for example, every day, once every two days, once every three days, etc. Alternatively or in addition, the culture can be monitored for specific medium components, for example, glucose and/or glutamine and/or any amino acid, and feedings can be adjusted so as to keep one or more of these components within a desired range. When compared to a batch culture, in which no feeding occurs, a fed batch culture can produce greater amounts of protein. See e.g. U.S. Pat. No. 5,672,502.

A feed medium of the invention will generally contain nutrients that are depleted during cell culture. A feed medium of the invention will typically contain most of the components of a typical mammalian base cell culture medium, but with some components, such as those generally viewed as nutrients, at high concentrations so as to avoid too much dilution of the culture. Particularly in culture used for protein production, it is advantageous to increase culture volume as little as possible with media feeds so as to maximize the amount of protein produced per unit volume. At large scale, an increase of, for example, fifty percent in volume, can create significant handling issues. A feed medium of the invention may contain many of amino acids found in a culture medium, but at, for example, about 5×, 6×, 7×, 8×, 9×, 10×, 12×, 14×, 16×, 20×, 30×, 50×, 100×, 200×, 400×, 600×, 800×, or even about 1000× of their usual concentration in a base medium. The amino acids can include alanine, arginine, asparagine, aspartate, cysteine, cystine, glutamate, glutamine, glycine, histidine, isoleucine, leucine, lysine, methionine, phenylalanine, proline, serine, threonine, tryptophan, tyrosine, and valine. As meant herein, such amino acids are the "L" stereoisomers commonly found in nature, rather than "D" stereoisomers, which are not commonly found in terrestrial living systems. For example, "cysteine" refers to L-cysteine rather than D-cysteine. Carbohydrates such as glucose or mannose, galactose, fructose, sucrose, or glucosamine, etc. can also be added to a feed medium of the invention or added a culture separately. Vitamins, proteins, serum, buffering agents, salts, and hydrolysates of soy, casein, and yeast may or may not be part of a feed medium of the invention. These feed media may be serum free. Feed media of the invention may or may not contain growth factors, such as IGF-1 or insulin. Feed media of the invention can be protein free and/or chemically defined, i.e., protein free, hydrolysate free, and serum free.

With regard to salts, such as, for example sodium chloride, the concentration used in a feed medium of the invention can be calculated such that the osmolarity of the culture does not go beyond an optimal range of from about 270 mOsm to about 550 mOsm or from about 270 mOsm to about 450 mOsm. In some embodiments, the osmolarity of the culture may range from about 250 mOsm to about to about 650 mOsm, or from about 260 mOsm to about 600 mOsm. The feed medium itself can have a wider range of osmolarity since it is diluted upon addition to the culture. Thus, a feed medium can have an osmolarity of from about 200 mOsm to about 1300 mOsm, from about 250 mOsm to about 1000 mOsm, from about 500 mOsm to about 1000 mOsm, from about 700 mOsm to about 900 mOsm, from about 270 mOsm to about 900 mOsm, from about 300 mOsm to about 830 mOsm, from about 200 mOsm to about 500 mOsm, or from about 200 mOsm to about 400 mOsm. Addition of a protein hydrolysate to a feed medium can contribute to higher osmolarity. Some salts may be omitted entirely from a feed medium. Thus, it is generally nutrients that are consumed during cell culture (such as amino acids and carbohydrates), rather than salts, buffers, or shear protectants, that are present in high concentrations in a feed medium.

Mammalian cells grown in culture generally can be cultured at near neutral pHs, such as from about pH 6.5 to about pH 7.5. Thus, although feed media of the invention can be somewhat outside this range, the addition of the feed medium will preferably not bring the pH of the entire culture outside this range. Thus, feed media can have a pH from about 5.8 to about 8.0, or from about 6.0 to about 7.8, or from about 6.1 to about 7.5, or from about 6.5 to about 7.4, from about 5.8 to about 7.4, or from about 6.0 to about 7.2. In some embodiments, the pH of a feed medium can be about 6.8, 6.9, 7.0, 7.1, or 7.2.

Most commonly-used components of mammalian culture feed medium are freely soluble in water. However, a few amino acids have limited solubility in water. For example L-cystine, an oxidized form of cysteine often used in culture media, is soluble at a concentration of up to only 0.112 g/L in water at 25° C., and L-tyrosine is soluble at a concentration of up to only 0.045 g/100 g of water (equivalent to 0.45 g/L) at 25° C. THE MERCK INDEX, $12^{th}$ Ed., Budavari et al., eds., Merck & Co., Inc., 1996, p. 471 and 9971. Cysteine readily oxidizes to form cystine in neutral or slightly alkaline aqueous solutions. Ibid, pp. 470-71. Thus, even though cysteine, itself, is freely water soluble, it may contribute to insolubility and/or precipitation of a medium in its oxidized form, cystine. Tyrosine is soluble in alkaline solutions, and cystine is quite soluble in solutions below pH 2 or above pH 8. Ibid, p. 471 and 9971. Since a feed medium is generally close to neutral pH, consistent with the requirements of mammalian cells, even moderate concentrations of tyrosine and/or cystine can present problems with medium stability. Furthermore, since cysteine can be oxidized to cystine in a neutral solution in the presence of air, cysteine may cause precipitation, even though cysteine, itself, is quite soluble in aqueous solutions. Thus, there is a need in the art for methods to stabilize feed media, which often contain high concentrations of amino acids such as cystine, tyrosine, and cysteine and have approximately neutral pH.

The concentration of pyruvate used in the feed media and methods of the invention can be at least about 0.9, 3, 5, 9, 10, 18, 20, 25, 30, 31, 32, 33, 34, 35, 36, 37, 38, 39, or 40 mM pyruvate and not more than about 40, 45, 50, 100, 200, or 315 mM pyruvate. Alternatively, the feed media of the invention can contain about 18, 20, 21, 22, 23, 24, 25, 26, 27, 28, 29, 30, 31, 32, 33, 34, 35, 36, 37, 38, 39, 40, or 45 mM pyruvate. The pyruvate concentration of the feed media can range from about 20 mM to about 315 mM, from about 20 mM to about 200 mM, from about 20 mM to about 100 mM, from about 20 mM to about 50 mM, from about 25 mM to about 45 mM, from about 25 mM to about 40 mM, or from about 30 mM to about 40 mM. The pyruvate can be sodium pyruvate.

The concentration of cysteine in a feed medium of the invention can be at least about 0.5, 1.0, 2.0, 3.0, 4.0, 5.0, 6.0, 7.0, 8.0, 9.0, 10.0, 11.0, 12.0, 14.0, 16.0, 18.0, or 20.0 mM and/or not more than about 8.0, 9.0, 10.0, 11.0, 12.0, 13.0, 14.0, 15.0, 16.0, 18.0, 20.0, 25.0, 30.0, 35.0, 40.0, 60.0 80.0, or 100.0 mM. Alternatively, the concentration of cysteine added to a feed medium of the invention can be from about 3 mM to about 40 mM, from about 5 mM to about 35 mM, from about 7 mM to about 30 mM, from about 8 mM to about 25 mM, or from about 7.5 mM to about 15 mM, or about 8, 10, 12, 14, 16, 18, or 20 mM.

Cystine can be present in a feed medium of the invention at a concentration from about 0.1 mM to about 2.5 mM, from about 0.5 mM to about 1.5 mM, from about 1.0 mM to about 1.2 mM, or about 1 mM or 1.1 mM. Alternatively, cystine can be added at a concentration of at least about 0.1, 0.2, 0.4, 0.5, 0.6, 0.8, or 1.0 mM and/or not more than 0.4, 0.6, 0.8, 1.0, 1.2, 1.4, 2, 3, 5, or 10 mM. Recognizing that some of the cysteine added to a medium may oxidize to form cystine or some of the cystine added to a medium may be reduced to form cysteine, the numbers given above for these concentrations refer to the concentration of cysteine or cystine which is actually added to the medium without later determination of what proportion of this may have been oxidized or reduced.

Either cysteine, cystine, or tyrosine may be omitted from a feed medium of the invention. Tyrosine may be present at less than or equal to about 4.6, 4.5, 4.4, 4.3, 4.2, or 4.1 mM. Tyrosine may be present in a concentration of at least about 0.5, 1.0, 1.5, 2.0, 2.5, 3.0, 3.5, or 4.0 mM. If present, tyrosine may be at a concentration greater than about 1 mM and less than about 4.4 or 4.6 mM, from about 2 mM to about 4.4 mM, from about 3 mM to about 4.0 mM, from about 3 mM to about 4.4 mM, or from about 4.0 mM to about 4.4 mM. Alternatively, tyrosine can be present in the feed media of the invention at about 3, 3.2, 3.4, 3.6, 3.8, 3.9, 4.0, 4.2, 4.4, or 4.5 mM.

A feed medium of the invention contains pyruvate, which can stabilize the medium. As explained above, a feed medium can also contain components such as cystine, cysteine, and tyrosine, which may destabilize the medium. Other components that are relatively insoluble in water may be included in a feed medium of the invention, provided that they are at concentrations such that the medium is stable for at least about 1, 2, or 3 weeks at room temperature. Some relatively insoluble components may form a separate, non-aqueous phase, and such components may or may not be included in a feed medium of the invention.

Table 1 (below) gives an exemplary list of the components that may be included in a feed medium of the invention and concentration ranges at which each component might be used. Depending on the needs of the cells, not all of these components need be present at all. Alternatively, a component may be present in a concentration outside of the ranges stated in Table 1. Moreover, components other than those listed in Table 1 can be included in a feed medium of the invention. Such additional medium components may, for example, include alanine, aspartate, glutamate, phenol red, or various vitamins including Vitamins A, D2, or B12 or ascorbic acid (Vitamin C) or alpha tocopherol phosphate, among many others.

TABLE 1

Composition of Exemplary Feed Media

| Feed Media Component | Concentration Range (mM) |
|---|---|
| L-Arginine | 1.0-57.0 |
| L-Asparagine | 8.0-200.0 |
| Biotin (B7) | 0.0003-0.05 |

TABLE 1-continued

Composition of Exemplary Feed Media

| Feed Media Component | Concentration Range (mM) |
| --- | --- |
| Calcium Chloride | 0.09-9.0 |
| D-Calcium Pantothenate | 0.02-2.1 |
| Choline Chloride | 0.008-55.0 |
| Cupric Sulfate | 0.00012-0.0012 |
| Cyanocobalamin (B12) | 0.01-0.6 |
| L-Cysteine | 2.1-105.0 |
| L-Cystine | 0.3-5.0 |
| Ferric Nitrate | 0.7-7.5 |
| Folic Acid | 0.02-2.3 |
| D-Glucose | Fed on demand |
| L-Glutamine | 8.2-206.0 |
| Glycine | 1.2-80.0 |
| L-Histidine | 0.6-67.0 |
| Hypoxanthine | 0.3-19.0 |
| i-Inositol | 0.1-59.0 |
| L-Isoleucine | 1.6-80.0 |
| L-Leucine | 2.2-115.0 |
| Linoleic Acid | 0.003-0.04 |
| DL-Alpha-Lipoic Acid | 0.01-1.0 |
| L-Lysine | 2.4-165.0 |
| Magnesium Chloride | 0.10-6.3 |
| Magnesium Sulfate | 0.81-12.5 |
| L-Methionine | 0.6-31.0 |
| Niacinamide (B3) | 0.05-2.5 |
| L-Phenylalanine | 0.7-46.0 |
| Potassium Chloride | 4.0-40.0 |
| Potassium Phosphate monobasic | 0.3-37.0 |
| Potassium Phosphate dibasic | 0.8-58.0 |
| L-Proline | 2.6-130 |
| Putrescine | 0.019-0.53 |
| Pyridoxal, HCl | 0.02-2.2 |
| Pyridoxine, HCl | 0.0005-0.2 |
| Riboflavin (B2) | 0.002-0.16 |
| L-Serine | 1.1-143.0 |
| Sodium bicarbonate | 0-30.0 |
| Sodium Chloride | As needed |
| Sodium Phos Dibas Anhy | 0.4-71.0 |
| Sodium Phos Monobas | 0.3-66.0 |
| Sodium Pyruvate | 3.0-454.0 |
| Thiamine (B1) | 0.003-1.4 |
| L-Threonine | 2.5-126.0 |
| Thymidine | 0.04-1.9 |
| L-Tryptophan | 0.2-11.0 |
| L-Tyrosine | 0.3-4.6 |
| L-Valine | 2.5-128.0 |
| Zinc Sulfate | 0.03-1.6 |

Proteins to be expressed by the cultured cells can be protein-based drugs, also known as biologics. The proteins can be secreted as extracellular products. The protein being produced can comprise part or all of a protein that is identical or substantially similar to a naturally-occurring protein, and/or it may, or may not, be a recombinant fusion protein. Optionally, the protein may be a human protein, a fragment thereof, or a substantially similar protein that is at least 15 amino acids in length. It may comprise a non-antibody protein and/or an antibody. It may be produced intracellularly or be secreted into the culture medium from which it can be recovered. It may or may not be a soluble protein.

The protein being produced can comprise part or all of a protein that is identical or substantially similar to a naturally-occurring protein, and/or it may, or may not, be a recombinant fusion protein. A recombinant fusion protein is a polypeptide that is a fusion of part of all of two different proteins. For example, the extracellular region of a receptor fused to the Fc region of an antibody is a recombinant fusion protein as meant herein. It may comprise a non-antibody protein and/or an antibody. It may be produced intracellularly or be secreted into the culture medium from which it can be recovered.

The media and methods of the invention can be used to produce just about any protein, and is particularly advantageous for proteins whose expression is under the control of a strong promoter, such as for example, a viral promoter, and/or proteins that are encoded on a message that has an adenoviral tripartite leader element. Examples of useful expression vectors that can be used to produce proteins are disclosed in International Application WO 01/27299 and in McMahan et al., (1991), EMBO J. 10: 2821, which describes the pDC409 vector. A protein is generally understood to be a protein of at least about 10 amino acids, optionally about 25, 75, or 100 amino acids.

The media and methods of the invention are useful for producing recombinant proteins. Some proteins that can be produced with the methods of the invention include proteins comprising amino acid sequences identical to or substantially similar to all or part of one of the following proteins: a flt3 ligand (as described in International Application WO 94/28391, incorporated herein by reference), a CD40 ligand (as described in U.S. Pat. No. 6,087,329 incorporated herein by reference), erythropoietin, thrombopoeitin, calcitonin, leptin, IL-2, angiopoietin-2 (as described by Maisonpierre et al. (1997), Science 277(5322): 55-60, incorporated herein by reference), Fas ligand, ligand for receptor activator of NF-kappa B (RANKL, as described in International Application WO 01/36637, incorporated herein by reference), tumor necrosis factor (TNF)-related apoptosis-inducing ligand (TRAIL, as described in International Application WO 97/01633, incorporated herein by reference), thymic stroma-derived lymphopoietin, granulocyte colony stimulating factor, granulocyte-macrophage colony stimulating factor (GM-CSF, as described in Australian Patent No. 588819, incorporated herein by reference), mast cell growth factor, stem cell growth factor (described in e.g. U.S. Pat. No. 6,204,363, incorporated herein by reference), epidermal growth factor, keratinocyte growth factor, megakaryote growth and development factor, RANTES, human fibrinogen-like 2 protein (FGL2; NCBI accession no. NM_00682; Rüegg and Pytela (1995), Gene 160: 257-62) growth hormone, insulin, insulinotropin, insulin-like growth factors, parathyroid hormone, interferons including α interferons, γ interferon, and consensus interferons (such as those described in U.S. Pat. Nos. 4,695,623 and 4,897,471, both of which are incorporated herein by reference), nerve growth factor, brain-derived neurotrophic factor, synaptotagmin-like proteins (SLP 1-5), neurotrophin-3, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS). Descriptions of proteins that can be produced according to the inventive methods may be found in, for example, *Human Cytokines: Handbook for Basic and Clinical Research, Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991), all of which are incorporated herein by reference.

Other proteins that can be produced using the media and methods of the invention include proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, as described in U.S. Pat. No. 5,395,760 and U.S. Pat. No. 5,610,279, both of which are incorporated herein by reference), Interleukin-1 (IL-1) receptors (types I and II; described in EP Patent No. 0 460 846, U.S. Pat. No. 4,968,607, and U.S. Pat. No. 5,767,064, all of which are incorporated herein by reference), IL-1 receptor antagonists (such as those described in U.S. Pat. No. 6,337,072, incorporated herein by reference), IL-1 antagonists or inhibitors (such as those described in U.S. Pat. Nos. 5,981,713, 6,096,728, and 5,075,222, all of which are incorporated herein by reference) IL-2 receptors, IL-4 receptors (as described in EP Patent No. 0 367 566 and U.S. Pat. No. 5,856,296, both of which are incorporated by reference), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, described in WO 01/36637 and U.S. Pat. No. 6,271,349, both of which are incorporated by reference), osteoprotegerin (described in e.g. U.S. Pat. No. 6,015,938, incorporated by reference), receptors for TRAIL (including TRAIL receptors 1, 2, 3, and 4), and receptors that comprise death domains, such as Fas or Apoptosis-Inducing Receptor (AIR).

Other proteins that can be produced using the media and methods of the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996, which is incorporated by reference). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand. Accordingly, members of the TNF and TNFR families can also be purified using the present invention.

Enzymatically active proteins or their ligands can also be produced using the media and methods of the invention. Examples include proteins comprising all or part of one of the following proteins or their ligands or a protein substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

The media and methods of the invention can also be used to produce antibodies, including human antibodies, or portions thereof and chimeric or humanized antibodies. Chimeric antibodies having human constant antibody immunoglobulin domains coupled to one or more murine variable antibody immunoglobulin domain, fragments thereof, or substantially similar proteins. Humanized antibodies contain variable regions comprising framework portions of human origin and CDR portion from a non-human source. The method of the invention may also be used to produce conjugates comprising an antibody and a cytotoxic or luminescent substance. Such substances include: maytansine derivatives (such as DM1); enterotoxins (such as a Staphlyococcal enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6). The invention can also be used to produce chimeric proteins selected in vitro to bind to a specific target protein and modify its activity such as those described in International Applications WO 01/83525 and WO 00/24782, both of which are incorporated by reference. Examples of antibodies, in vitro-selected chimeric proteins, or antibody/cytotoxin or antibody/luminophore conjugates that can be produced by the methods of the invention include those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (such as those described in U.S. Pat. Nos. 5,272,064 and 5,149,792), VEGF, TGF, TGF-β2, TGF-β1, EGF receptor (including those described in U.S. Pat. No. 6,235,883 B1, incorporated by reference) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19-25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphlycoccus aureus*.

The media and methods of the invention may also be used to produce all or part of an anti-idiotypic antibody or a substantially similar protein, including anti-idiotypic antibodies against: an antibody targeted to the tumor antigen gp72; an antibody against the ganglioside GD3; an antibody against the ganglioside GD2; or antibodies substantially similar to these.

The media and methods of the invention can also be used to produce recombinant fusion proteins comprising any of the above-mentioned proteins. For example, recombinant fusion proteins comprising one of the above-mentioned proteins plus a multimerization domain, such as a leucine zipper, a coiled coil, an Fc portion of an antibody, or a substantially similar protein, can be produced using the methods of the invention. See e.g. WO94/10308; Lovejoy et al. (1993), Science 259:1288-1293; Harbury et al. (1993), Science 262: 1401-05; Harbury et al. (1994), Nature 371:80-83; Håkansson et al. (1999), Structure 7:255-64, all of which are incorporated by reference. Specifically included among such recombinant fusion proteins are proteins in which a portion of TNFR or RANK is fused to an Fc portion of an antibody (TNFR:Fc or RANK:Fc). TNFR:Fc comprises the Fc portion of an antibody fused to an extracellular domain of TNFR, which includes amino acid sequences substantially similar to amino acids 1-163, 1-185, or 1-235 of FIG. 2A of U.S. Pat. No. 5,395,760, which is incorporated by reference. RANK: Fc is described in International Application WO 01/36637, which is incorporated by reference.

Preferably, the proteins are expressed under the control of a heterologous control element such as, for example, a promoter that does not in nature direct the production of that protein. For example, the promoter can be a strong viral promoter (e.g., CMV, SV40) that directs the expression of a mammalian protein. The host cell may or may not normally produce the protein. For example, the host cell can be a CHO cell that has been genetically engineered to produce a human protein, meaning that nucleic acid encoding the human protein has been introduced into the CHO cell. Alternatively, the host cell can be a human cell that has been genetically engineered to produce increased levels of a human protein normally present only at very low levels (e.g., by replacing the endogenous promoter with a strong viral promoter). For the production of recombinant proteins, an expression vector encoding the recombinant protein can be transferred, for example by transfection or viral infection, into a substantially homogeneous culture of host cells. The expression vector, which can be constructed using the methods of genetic engineering, can include nucleic acids encoding the protein of interest operably linked to suitable regulatory sequences.

The regulatory sequences are typically derived from mammalian, microbial, viral, and/or insect genes. Examples of regulatory sequences include transcriptional promoters, operators, and enhancers, a ribosomal binding site (see e.g. Kozak (1991), J. Biol. Chem. 266:19867-19870), appropriate sequences to control transcriptional and translational initiation and termination, polyadenylation signals (see e.g. McLauchlan et al. (1988), Nucleic Acids Res. 16:5323-33), and matrix and scaffold attachment sites (see Phi-Van et al. (1988), Mol. Cell. Biol. 10:2302-07; Stief et al. (1989), Nature 341:342-35; Bonifer et al. (1990), EMBO J. 9:2843-38). Nucleotide sequences are operably linked when the regulatory sequence functionally relates to the protein coding sequence. Thus, a promoter nucleotide sequence is operably linked to a protein coding sequence if the promoter nucleotide sequence controls the transcription of the coding sequence. A gene encoding a selectable marker is generally incorporated into the expression vector to facilitate the identification of recombinant cells.

Transcriptional and translational control sequences for mammalian host cell expression vectors can be excised from viral genomes. Commonly used promoter and enhancer sequences are derived from polyoma virus, adenovirus 2, simian virus 40 (SV40), and human cytomegalovirus (CMV). For example, the human CMV promoter/enhancer of immediate early gene 1 may be used. See e.g. Patterson et al. (1994), Applied Microbiol. Biotechnol. 40:691-98. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al. (1978), Nature 273:113; Kaufman (1990), Meth. in Enzymol. 185:487-511). Smaller or larger SV40 fragments can also be used, provided the approximately 250 bp sequence extending from the Hind III site toward the Bgl I site located in the SV40 viral origin of replication site is included.

In addition, a sequence encoding an appropriate native or heterologous signal peptide (leader sequence) can be incorporated into the expression vector, to promote extracellular secretion of the recombinant protein. The signal peptide will be cleaved from the recombinant protein upon secretion from the cell. The choice of signal peptide or leader depends on the type of host cells in which the recombinant protein is to be produced. Examples of signal peptides that are functional in mammalian host cells include the signal sequence for interleukin-7 (IL-7) described in U.S. Pat. No. 4,965,195, the signal sequence for interleukin-2 receptor described in Cosman et al. (1984), Nature 312:768; the interleukin-4 receptor signal peptide described in EP Patent No. 367,566; the type I interleukin-1 receptor signal peptide described in U.S. Pat. No. 4,968,607; and the type II interleukin-1 receptor signal peptide described in EP Patent No. 0 460 846.

Established methods for introducing DNA into mammalian cells have been described. Kaufman, R. J., Large Scale Mammalian Cell Culture, 1990, pp. 15-69. Additional protocols using commercially available reagents, such as the cationic lipid reagents LIPOFECTAMINE™, LIPOFECTAMINE™-2000, or LIPOFECTAMINE™-PLUS (which can be purchased from Invitrogen), can be used to transfect cells. Felgner et al. (1987)., Proc. Natl. Acad. Sci. USA 84:7413-7417. In addition, electroporation or bombardment with microprojectiles coated with nucleic acids can be used to transfect mammalian cells using procedures, such as those in Sambrook et al., Molecular Cloning: A Laboratory Manual, 2nd ed. Vol. 1-3, Cold Spring Harbor Laboratory Press (1989) and Fitzpatrick-McElligott (1992), Biotechnology (NY) 10(9):1036-40. Selection of stable transfectants can be performed using methods known in the art, such as, for example, resistance to cytotoxic drugs. Kaufman et al. ((1990), Meth. in Enzymology 185:487-511), describes several selection schemes, such as dihydrofolate reductase (DHFR) resistance. A suitable host strain for DHFR selection can be CHO strain DX-B11, which is deficient in DHFR. Urlaub and Chasin (1980), Proc. Natl. Acad. Sci. USA 77:4216-4220. A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Additional control sequences shown to improve expression of heterologous genes from mammalian expression vectors include such elements as the expression augmenting sequence element (EASE) derived from CHO cells (Morris et al., in Animal Cell Technology, pp. 529-534 (1997); U.S. Pat. Nos. 6,312,951 B1, 6,027,915, and 6,309,841 B1) and the tripartite leader (TPL) and VA gene RNAs from Adenovirus 2 (Gingeras et al. (1982), J. Biol. Chem. 257:13475-13491). The internal ribosome entry site (IRES) sequences of viral origin allows dicistronic mRNAs to be translated efficiently (Oh and Sarnow (1993), Current Opinion in Genetics and Development 3:295-300; Ramesh et al. (1996), Nucleic Acids Research 24:2697-2700). Expression of a heterologous cDNA as part of a dicistronic mRNA followed by the gene for a selectable marker (e.g. DHFR) has been shown to improve transfectability of the host and expression of the heterologous cDNA (Kaufman et al. (1990), Methods in Enzymol. 185: 487-511). Exemplary expression vectors that employ dicistronic mRNAs are pTR-DC/GFP described by Mosser et al., Biotechniques 22:150-161 (1997), and p2A5I described by Morris et al., in Animal Cell Technology, pp. 529-534 (1997).

A useful high expression vector, pCAVNOT, has been described by Mosley et al. ((1989), *Cell* 59:335-348). Other expression vectors for use in mammalian host cells can be constructed as disclosed by Okayama and Berg ((1983), Mol. Cell. Biol. 3:280). A useful system for stable high level expression of mammalian cDNAs in C127 murine mammary epithelial cells can be constructed substantially as described by Cosman et al. ((1986), Mol. Immunol. 23:935). A useful high expression vector, PMLSV N1/N4, described by Cosman et al. ((1984), Nature 312:768), has been deposited as ATCC 39890. Additional useful mammalian expression vectors are described in EP Patent No.-A-0 367 566 and WO 01/27299 A1. The vectors can be derived from retroviruses. Further, other vectors, such as those described by Aldrich et al. (Biotechnol. Prog. 19: 1433-38 (2003)) or by Bianchi and McGrew (Biotechnol. Bioeng. 84: 439-44 (2003)), may be used.

In place of the native signal sequence, a heterologous signal sequence can be added, such as one of the following sequences: the signal sequence for IL-7 described in U.S. Pat. No. 4,965,195; the signal sequence for IL-2 receptor described in Cosman et al. (Nature 312:768 (1984)); the IL-4 signal peptide described in EP Patent No. 0 367 566; the type I IL-1 receptor signal peptide described in U.S. Pat. No. 4,968,607; and the type II IL-1 receptor signal peptide described in EP Patent No. 0 460 846.

The proteins can be produced recombinantly in eukaryotic cells and can be secreted by host cells adapted to grow in cell culture. Optionally, host cells for use in the invention are mammalian cells. The cells can be also genetically engineered to express a gene of interest, can be mammalian production cells adapted to grow in cell culture, and/or can be homogenous cell lines. Examples of such cells commonly used in the industry are VERO, BHK, HeLa, CV1 (including Cos), MDCK, 293, 3T3, myeloma cell lines (e.g., NSO, NS1), PC12, WI38 cells, and Chinese hamster ovary (CHO) cells, which are widely used for the production of several complex recombinant proteins, e.g. cytokines, clotting factors, and antibodies (Brasel et al. (1996), Blood 88:2004-2012; Kaufman et al. (1988), J. Biol Chem 263:6352-6362; McKinnon et al. (1991), J Mol Endocrinol 6:231-239; Wood et al. (1990), J. Immunol. 145:3011-3016). The dihydrofolate reductase (DHFR)-deficient mutant cell lines (Urlaub et al. (1980), Proc Natl Acad Sci USA 77: 4216-4220, which is incorporated by reference), DXB11 and DG-44, are desirable CHO host cell lines because the efficient DHFR selectable and amplifiable gene expression system allows high level recombinant protein expression in these cells (Kaufman R. J. (1990), Meth Enzymol 185:537-566, which is incorporated by reference). In addition, these cells are easy to manipulate as adherent or suspension cultures and exhibit relatively good genetic stability. CHO cells and recombinant proteins expressed in them have been extensively characterized and have been approved for use in clinical commercial manufacturing by regulatory agencies. The methods of the invention can also be practiced using hybridoma cell lines that produce an antibody. Methods for making hybridoma lines are well known in the art. See e.g. Berzofsky et al. in Paul, ed., *Fundamental Immunology, Second Edition*, pp. 315-356, at 347-350, Raven Press Ltd., New York (1989). Cell lines derived from the above-mentioned lines are also suitable for practicing the invention.

According to the present invention, a eukaryotic, optionally a mammalian, host cell is cultured under conditions that promote the production of the protein of interest, which can be any protein, including an antibody or a recombinant protein. The culture is fed using the concentrated feed media and methods of the invention.

Cell culture medium formulations for use as base media are well known in the art. To these basal culture medium formulations the skilled artisan will add components such as amino acids, salts, sugars, vitamins, hormones, growth factors, buffers, antibiotics, lipids, trace elements and the like, depending on the requirements of the host cells to be cultured. The culture medium may or may not contain serum and/or protein. Various tissue culture media, including serum-free and/or defined culture media, are commercially available for cell culture. Tissue culture media is defined, for purposes of the invention, as a media suitable for growth of eukaryotic cells, and optionally mammalian cells, in in vitro cell culture. Typically, tissue culture media contains a buffer, salts, energy source, amino acids, vitamins and trace essential elements. Any media capable of supporting growth of the appropriate eukaryotic cell in culture can be used; the invention is broadly applicable to eukaryotic cells in culture, particularly mammalian cells, and the choice of media is not crucial to the invention. Tissue culture media suitable for use as a base medium, as defined herein, in the methods of the invention are commercially available from, e.g., ATCC (Manassas, Va.). For example, any one or combination of the following media can be used as a base medium: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (available from SAFC Biosciences, which was formerly JRH Biosciences, Lenexa, Kans., USA), among others, which can be obtained from the American Type Culture Collection or SAFC Biosciences, as well as other vendors. When defined medium that is serum-free and/or peptone-free is used, the medium is usually highly enriched for amino acids and trace elements. See, for example, U.S. Pat. No. 5,122,469 to Mather et al. and U.S. Pat. No. 5,633,162 to Keen et al. Peptone or other protein hydrolysates can be added to a culture medium.

Cell culture media, including base media and/or feed media, can be serum-free, protein-free, growth factor-free, and/or peptone-free media. The term "serum-free" as applied to media includes any mammalian cell culture medium that does not contain serum, such as fetal bovine serum. The term "insulin-free" as applied to media includes any medium to which no exogenous insulin has been added. By exogenous is meant, in this context, other than that produced by the culturing of the cells themselves. The term "IGF-1-free" as applied to media includes any medium to which no exogenous Insulin-like growth factor-1 (IGF-1) or analog (such as, for example, LongR3, [Ala31], or [Leu24][Ala31] IGF-1 analogs available from Novozymes GroPep Ltd. of Thebarton, South Australia) has been added. The term "growth-factor free" as applied to media includes any medium to which no exogenous growth factor (e.g., insulin, IGF-1) has been added. The term "protein-free" as applied to media includes medium free from exogenously added protein, such as, for example, transferrin and the protein growth factors IGF-1 and insulin. Protein-free media may or may not have peptones. The term "peptone-free" as applied to media includes any medium to which no exogenous protein hydrolysates have been added such as, for example, animal and/or plant protein hydrolysates. Eliminating peptone from media has the advantages of reducing lot to lot variability and enhancing processing steps, such as filtration. Chemically defined media are media in which every component is defined and obtained from a pure source, preferably a non-animal source.

The skilled artisan may also choose to use one of the many individualized base media formulations that have been developed to maximize cell growth, cell viability, and/or recombinant protein production in a particular cultured host cell. The methods according to the current invention may be used in combination with commercially available cell culture media or with a cell culture medium that has been individually formulated for use with a particular cell line. For example, an enriched base medium that could support increased protein production may comprise a mixture of two or more commercial media, such as, for instance, DMEM and Ham's F12 media combined in ratios such as, for example, 1:1, 1:2, 1:3, 1:4, 1:5, 1:6, 1:7, 1:8, or even up to 1:15 or higher. Alternatively or in addition, a base medium can be enriched by the addition of nutrients, such as amino acids or peptone, and/or a medium (or most of its components with the exceptions noted below) can be used at greater than its usual, recommended concentration, for example at about 2×, 3×, 4×, 5×, 6×, 7×, 8×, or even higher concentrations. As used herein, "1×" means the standard concentration normally used in a particular base medium. "2×" means twice the standard concentration, etc. In any of these embodiments, medium components that can substantially affect osmolarity, such as salts, cannot be increased in concentration so that the osmolarity of the culture falls outside of an acceptable range, such as, for example about 200-700 mOsm, or, more typically, about 270 mOsm to about 400 mOsm. Thus, a base medium may, for example, be 8× with respect to all components except salts, which can be present at only 1×. An enriched medium may be serum free and/or protein free. A serum free medium lacks serum, such as, for example, bovine serum, which is commonly used in cell culture. Further, a base medium may be supplemented periodically with a feed medium of the invention during the time a culture is maintained to replenish medium components that can become depleted such as, for example, vitamins, amino acids, and metabolic precursors. As is known in the art, different media and temperatures may have somewhat different effects on different cell lines, and the same medium and temperature may not be suitable for all cell lines.

Concentrated feed media of the invention can be based on just about any base culture medium. Such a concentrated feed medium can contain many of the components of the culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount. However, not all components of a standard medium can be increased in concentration in a concentrated feed medium to the same extent, if at all. For example, in a 10× concentrated feed medium, salts such as sodium chloride or iron salts might be present at only 1× or be entirely absent. Using them at 10× concentration could bring the osmolarity of the medium into an unacceptable range. An acceptable osmotic range can be from about 200-1500 mOsm. Similarly, some medium components are not substantially depleted during cell growth and, thus, need not be present at increased concentrations, or, in some cases need not be present at all, in a feed medium. Guided by these considerations, one of skill in the art could readily design a concentrated feed medium based on any known eukaryotic, especially mammalian, base culture medium.

As is known in the art the solubility and stability of a concentrated feed medium can be very substantially affected by relatively insoluble medium components, such as tyrosine and cystine, or by medium components that readily convert to insoluble species, such as cysteine. As shown in Example 1, tyrosine and cysteine can be important for increasing protein production by a culture. Thus, it can be desirable to include such insoluble species at high concentrations in a feed medium. The media and methods of the invention provide a means, i.e., the addition of high concentrations of sodium pyruvate, of stabilizing media containing high concentrations of cysteine and/or cystine and/or tyrosine.

Suitable culture conditions for mammalian cells are known in the art. See e.g. Animal cell culture: A Practical Approach, D. Rickwood, ed., Oxford university press, New York (1992). Mammalian cells may be cultured in suspension or while attached to a solid substrate. Furthermore, mammalian cells may be cultured, for example, in fluidized bed bioreactors, hollow fiber bioreactors, roller bottles, shake flasks, or stirred tank bioreactors, with or without microcarriers, and operated in a batch, fed batch, continuous, semi-continuous, or perfusion mode. The media and methods of the invention specifically involve a method in which concentrated feed medium is added to the culture either continuously or at intervals during the culture. For example, a culture may be fed, for example, once per day, every other day, every three days, every four days, every five days, or may be fed when the concentration of a specific medium component, which is being monitored, falls outside a desired range. Alternatively, a culture may be fed on an irregular schedule, for example on days 2, 5, and 7.

The methods according to the present invention may be used to improve the production of recombinant proteins in both single phase and multiple phase culture processes. In a single phase process, cells are inoculated into a culture environment and the disclosed methods are employed during the single production phase. In a multiple stage process, cells are cultured in two or more distinct phases. For example cells may be cultured first in one or more growth phases, under environmental conditions that maximize cell proliferation and viability, then transferred to a production phase, under conditions that maximize protein production. In a commercial process for production of a protein by mammalian cells, there are commonly multiple, for example, at least about 2, 3, 4, 5, 6, 7, 8, 9, or 10 growth phases that occur in different culture vessels preceding a final production phase. The growth and production phases may be preceded by, or separated by, one or more transition phases. In multiple phase processes, the methods according to the present invention can be employed at least during the production phase, although they may also be employed in a preceding growth phase. A production phase can be conducted at large scale. A large scale process can be conducted in a volume of at least about 100, 500, 1000, 2000, 3000, 5000, 7000, 8000, 10,000, 15,000, 20,000 liters, or larger. A growth phase may occur at a higher temperature than a production phase. For example, a growth phase may occur at a first temperature from about 35° C. to about 39° C., and a production phase may occur at a second temperature from about 29° C. to about 39° C., optionally from about 30° C. to about 36° C. or from about 30° C. to about 34° C. Chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift.

The methods of the invention can be used to culture cells that produce a protein, and the resulting expressed protein can then be collected. In addition, the protein can be purified, or partially purified, from such a culture (e.g., from culture medium or cell extracts) using known processes. By "partially purified" means that some fractionation procedure, or procedures, have been carried out, but that more protein species (at least 10%) than the desired protein is present. By "purified" is meant that the protein is essentially homogeneous, i.e., less than about 2% contaminating proteins are present. Fractionation procedures can include but are not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above.

For example, the purification of the protein can include an affinity column containing agents which will bind to the protein; one or more column steps over such affinity resins as concanavalin A-agarose, heparin-TOYOPEARL® (Toyo Soda Manufacturing Co., Ltd., Japan) or Cibacrom blue 3GA SEPHAROSE® (Pharmacia Fine Chemicals, Inc., New York); one or more steps involving elution; and/or immunoaffinity chromatography. The protein can be expressed in a form that facilitates purification. For example, it may be expressed as a fusion protein, such as those of maltose binding protein (MBP), glutathione-S-transferase (GST), or thioredoxin (TRX). Kits for expression and purification of such fusion proteins are commercially available from New England BioLab (Beverly, Mass.), Pharmacia (Piscataway, N.J.) and InVitrogen, respectively. The protein can be tagged with an epitope and subsequently purified by using a specific antibody directed to such epitope. One such epitope (FLAG®) is commercially available from Kodak (New Haven, Conn.). It is also possible to utilize an affinity column comprising a protein-binding protein, such as a monoclonal antibody to the recombinant protein, to affinity-purify expressed proteins. Other types of affinity purification steps can be a Protein A or a Protein G column, which affinity agents bind to proteins that contain Fc domains. Proteins can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety.

The desired degree of final purity depends on the intended use of the protein. A relatively high degree of purity is desired when the protein is to be administered in vivo, for example. In such a case, the proteins are purified such that no protein bands corresponding to other proteins are detectable upon analysis by SDS-polyacrylamide gel electrophoresis (SDS-PAGE). It will be recognized by one skilled in the pertinent field that multiple bands corresponding to the protein can be visualized by SDS-PAGE, due to differential glycosylation, differential post-translational processing, and the like. Optionally, the protein of the invention is purified to substantial homogeneity, as indicated by a single protein band upon analysis by SDS-PAGE. The protein band can be visualized by silver staining, Coomassie blue staining, or (if the protein is radiolabeled) by autoradiography.

The invention also optionally encompasses further formulating the proteins. By the term "formulating" is meant that the proteins can be buffer exchanged, sterilized, bulk-packaged, and/or packaged for a final user. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the protein, in combination with other components such as a physiologically acceptable diluent, carrier, or excipient. The term "physiologically acceptable" means a non-toxic material that does not interfere with the effectiveness of the biological activity of the active ingredient(s).

Formulations suitable for administration include aqueous and non-aqueous sterile injection solutions which may contain anti-oxidants, buffers, bacteriostats, and solutes which render the formulation isotonic with the blood of the recipient; and aqueous and non-aqueous sterile suspensions which may include suspending agents or thickening agents. The proteins can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants, and/or carriers. Suitable formulations for pharmaceutical compositions include those described in Remington's Pharmaceutical Sciences, 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871, 4,501,728, 4,837,028, and 4,737,323. Such compositions will influence the physical state, solubility, stability, rate of in vivo release, and rate of in vivo clearance, and are thus chosen according to the intended application, so that the characteristics of the carrier will depend on the selected route of administration. Sustained-release forms suitable for use include, but are not limited to, proteins that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

All references cited herein are incorporated by reference herein in their entirety. The invention having been described, the following examples are offered by way of illustration, and not limitation.

EXAMPLES

Example 1

Addition of Tyrosine and Cysteine Increases Protein Titers

A CHO cell line producing a recombinant protein was cultured in a commercially available base medium (a modified version of the EX-CELL™ 325 PF CHO serum free medium of catalog number 24340C from SAFC Biosciences (Lenexa, Kans.) in which the sodium chloride concentration is 4.5 g/L, rather than the 6.508 g/L present in catalog number 24340C) and fed with Feed Medium A with or without cysteine and/or tyrosine. Feed Medium A was designed based on the standard, commercially available medium, DMEM. DMEM is commercially available from, for example, American Type Culture Collection, Manassas, Va., USA. Feed Medium A contained all of the ingredients listed in Table 1 within the concentration ranges listed in Table 1 except the following ingredients, which were not part of Feed Medium A: arginine, asparagine, biotin, calcium chloride, cupric sulfate, cyanocobalamin, cysteine, cystine, glucose (which was added separately), hypoxanthine, linoleic acid, alpha-lipoic acid, magnesium chloride, niacinamide, potassium chloride, potassium phosphate monobasic, potassium phosphate disbasic, proline, putrescine, pyridoxal, riboflavin, sodium phosphate dibasic, sodium pyruvate, thymidine, tyrosine, and zinc sulfate. The amount of sodium chloride in Feed Medium A was adjusted so as to bring the osmolarity of the medium to about 300 mOsm.

To Feed Medium A, cysteine, tyrosine, and sodium pyruvate were added in varying combinations. The feed media differed only in their concentrations of tyrosine, cysteine, and sodium pyruvate, which are shown in Table 2 below. The feed media were mixed at room temperature. The cells were cultured in 125 ml shaker flasks with vented caps in the base medium described above. The shakers flasks were maintained at 36° C. in 5% $CO_2$. Flasks were agitated at 150 rpm. All flasks were seeded $5 \times 10^5$ cells per ml in a volume of 30 ml volume. On days 3, 6, and 8, 0.1 culture volume of each the feed media described in Table 2 were added to one of the four flasks. Day 0 is the day the cultures were started, day 1 is the first day thereafter, day 2 is the second day thereafter, etc. Protein titer was determined at days 8 and 10.

TABLE 2

Concentrations of Medium Components

| Feed Medium | Tyrosine (mM) | Cysteine (mM) | Sodium pyruvate (mM) |
|---|---|---|---|
| #1 | 0.0 | 0.0 | 0.0 |
| #2 | 0.0 | 0.0 | 36.35 |
| #3 | 4.40 | 12.53 | 0.0 |
| #4 | 4.40 | 12.53 | 36.35 |

Figure 1:
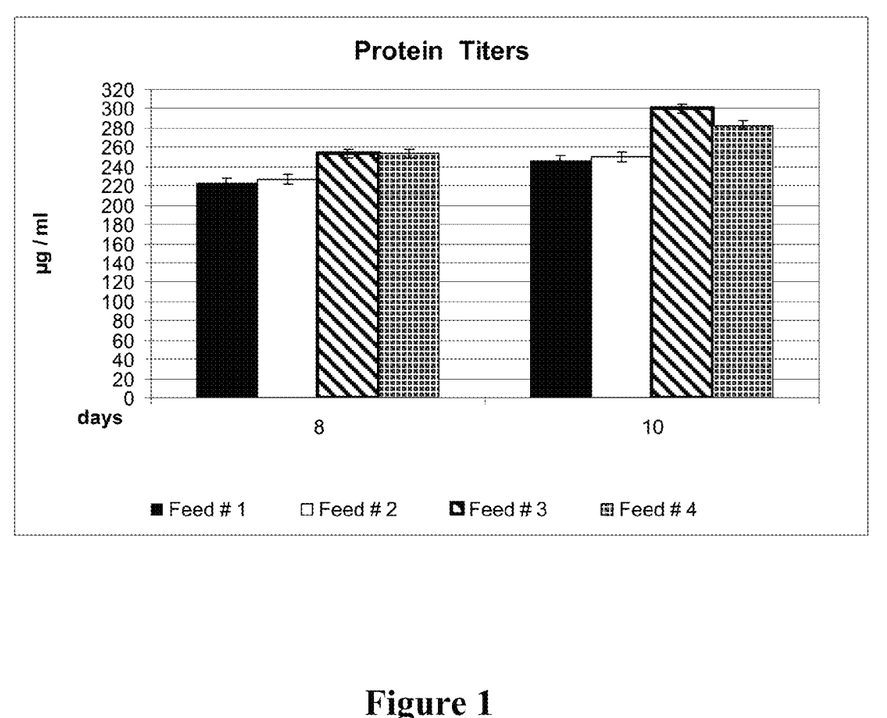
FIG. 1: Protein titers at 8 (left) or 10 (right) days of culture are indicated by the bars. The cells are CHO cells producing a recombinant protein. The cells were cultured as described in Example 1 and fed with a feed media as described in Example 1 and Table 2.

FIG. 1 shows the protein titers observed on days 8 and 10 of the culture. These data indicate that the addition of tyrosine and cysteine to Feed Medium A increases protein titer. Thus, adding cysteine and tyrosine to a feed medium can be advantageous. Hence, methods for keeping these medium components in solution can be advantageous, particularly for large volumes of feed media and/or in situations where it is most convenient to make feed media somewhat in advance of its actual use.

Example 2

High Concentrations of Pyruvate Stabilize Concentrated Feed Media Containing Tyrosine, Cysteine, and Cystine Feed Medium B is a concentrated feed medium. It contains all of the ingredients listed in Table 1 within the concentration ranges listed in Table 1 except the following ingredients, which were not part of Feed Medium B: arginine, glucose (which is added to the culture separately), and ferric nitrate. Feed Medium B contains 1 mM cystine, 3.03 mM tyrosine, 3.5 mM sodium pyruvate, and 7 mM cysteine. Feed Medium B required heating to 45° C. in order to dissolve all medium components, and it typically formed a precipitate upon storage for a few days at room temperature or at 4-8° C. This characteristic made its use, especially for a large-scale commercial culture for production of a biologic, certainly very inconvenient, if not potentially impractical.

To circumvent the issues of insolubility and instability, tyrosine and cystine were eliminated from the Feed Medium B. The resulting medium, Feed Medium C, did not require heating in order to dissolve and did not precipitate within 28 days of storage at 4° C. Thus, tyrosine and/or cystine are likely responsible for the insolubility and instability of Feed Medium B.

Varying concentrations of sodium pyruvate were added to Feed Medium B to determine whether Feed Medium B could be stabilized by pyruvate. The media were stored at 4-8° C. and were checked for stability on days 3, 6, and 8, where day 0 is the day the medium is made and day 1 is the next day. The volume of each sample was 50 ml. Table 3 below shows the concentrations of cysteine, cystine, tyrosine, and pyruvate in each tested medium.

TABLE 3

Concentrations of medium components and stability of media

| Cysteine (mM) | Cystine (mM) | Tyrosine (mM) | Pyruvate (mM) |
|---|---|---|---|
| 7.00 | 1.0 | 3.03 | 3.50 |
| 7.00 | 1.0 | 3.03 | 11.36 |
| 7.00 | 1.0 | 3.03 | 14.00 |
| 7.00 | 1.0 | 3.03 | 19.27 |
| 7.00 | 1.0 | 3.03 | 35.00 |

On day 3, the sample containing 3.5 mM pyruvate contained more precipitate than any other, followed by the sample containing 11.36 mM pyruvate and by the sample containing 14 mM pyruvate. Samples containing 19.27 and 35 mM pyruvate did not contain precipitate after one week of storage. However, the sample containing 19.27 mM pyruvate did contain a precipitate when it was discarded some weeks later. The sample containing 35 mM pyruvate was still without precipitate at this time. These data indicate that a concentration of 19.27 mM is adequate to stabilize Feed Medium B for at least one week and that a concentration of 35 mM pyruvate can stabilize Feed Medium B somewhat longer that one week.

Example 3

Stabilizing a Feed Medium Containing Tyrosine and Cysteine

In order to produce a stable medium containing tyrosine, varying concentrations of pyruvate and tyrosine were added to Feed Medium C. These concentrations are shown in Table 4 below. Feed Medium C, contains all the ingredients listed in Table 1 within the concentration ranges listed in Table 1 except the following ingredients, which were not part of Feed Medium C: arginine, cystine, glucose (which is added to the culture separately), ferric nitrate, and tyrosine. Thus, as mentioned above, the only difference between Feed Media B and C is the absence of cystine and tyrosine in Feed Medium C. The concentration of cysteine in Feed Medium C is 7 mM.

Stability during storage was tested. The media were stored at 4-8° C. The media were evaluated for precipitation by visual inspection on days 0, 1, 2, 5, 6, 7, 8, 9, 12, 13, 14, 15, 16, 19, 20, 21, 22, 23, and 28, where day 0 is the day the media was made, day 1 is the first day thereafter, day 2 is the second day thereafter, etc. Media samples scored "none" in the rightmost column of Table 4 did not contain any precipitate while this experiment was ongoing, that is, for 28 days. For samples that did precipitate during the course of the experiment, the first day on which a precipitate was observed is recorded in the rightmost column of Table 4.

TABLE 4

Stabilizing effects of sodium pyruvate at varying concentrations of tyrosine

| Media | Tyrosine concentration (mM) | Sodium pyruvate concentration (mM) | Day on which precipitate was first noted |
|---|---|---|---|
| Feed Medium C | 0 | 3.5 | none |
| Feed Medium C | 3.03 | 3.5 | none |
| Feed Medium C | 3.03 | 35.0 | none |
| Feed Medium C | 4.40 | 3.5 | 19 |
| Feed Medium C | 4.40 | 35.0 | none |
| Feed Medium C | 5.74 | 3.5 | 9 |
| Feed Medium C | 5.74 | 35.0 | 6 |

These data indicate that 35 mM sodium pyruvate stabilizes Feed Medium C when it contains 4.4 mM tyrosine, whereas the lower pyruvate concentration, 3.5 mM, does not. However, addition of 3.03 mM tyrosine did not destabilize the medium, and even feed medium containing 4.4 mM tyrosine was stable for a considerable period when it contained 3.5 mM pyruvate. No concentration of pyruvate tested stabilized medium containing 5.74 mM tyrosine.

Example 4

Effects of Cysteine, Cystine, Tyrosine, Pyruvate, and Storage Temperature on Medium Stability The following experiment explores interactions of various parameters and their effects on the stability of Feed Medium C. Feed Medium C (which is described in Examples 2 and 3) was prepared, and tyrosine, sodium pyruvate, cysteine, and cystine were added, or not, to various media samples. All media were mixed at room temperature. Stability was assessed at either room temperature or 4-8° C. The samples were visually inspected on days 0, 2, 5, 7, 9, 12, 14, 16, 19, 20, 23, and 26 of storage to determine whether precipitates had formed. Table 5 below lists the storage temperatures (where "RT" means room temperature) and the concentrations of cysteine, cystine, tyrosine, and sodium pyruvate in each sample. Samples are scored for precipitate as explained in Example 3, except that "none" in the rightmost column means that there was no precipitate for the 26 days (rather than the 28 days) that the experiment was ongoing.

TABLE 5

Stability and composition of media

| L-Cysteine (mM) | L-Tyrosine (mM) | Sodium Pyruvate (mM) | L-Cystine (mM) | Storage Temperature | pH | Osmo (mOsm) | Day on which precipitate was first noted |
|---|---|---|---|---|---|---|---|
| 7.0 | 0.0 | 3.5 | 0.0 | RT | 6.52 | 238 | none |
| 7.0 | 0.0 | 35.0 | 1.0 | RT | 6.19 | 294 | none |
| 7.0 | 4.4 | 3.5 | 1.0 | RT | 7.06 | 252 | 2 |
| 7.0 | 4.4 | 35.0 | 0.0 | RT | 6.87 | 307 | none |
| 16 | 0.0 | 3.5 | 1.0 | RT | 6.01 | 263 | 2 |
| 16 | 0.0 | 35.0 | 0.0 | RT | 6.01 | 303 | none |
| 16 | 4.4 | 3.5 | 0.0 | RT | 6.48 | 271 | 2 |
| 16 | 4.4 | 35.0 | 1.0 | RT | 6.01 | 308 | none |
| 7.0 | 0.0 | 3.5 | 1.0 | RT | 6.52 | 238 | 2 |
| 7.0 | 0.0 | 35.0 | 0.0 | RT | 6.31 | 283 | none |
| 7.0 | 4.4 | 3.5 | 0.0 | RT | 7.11 | 250 | none |
| 7.0 | 4.4 | 35.0 | 1.0 | RT | 6.83 | 289 | none |
| 16 | 0.0 | 3.5 | 0.0 | RT | 6.26 | 256 | 2 |
| 16 | 0.0 | 35.0 | 1.0 | RT | 6.01 | 299 | none |
| 16 | 4.4 | 3.5 | 1.0 | RT | 6.39 | 262 | 2 |
| 16 | 4.4 | 35.0 | 0.0 | RT | 6.01 | 317 | none |
| 7.0 | 0.0 | 3.5 | 1.0 | 4-8° C. | 6.51 | 237 | 2 |
| 7.0 | 0.0 | 35.0 | 0.0 | 4-8° C. | 6.32 | 284 | none |
| 7.0 | 4.4 | 3.5 | 0.0 | 4-8° C. | 7.07 | 252 | 23 |
| 7.0 | 4.4 | 35.0 | 1.0 | 4-8° C. | 6.81 | 294 | none |
| 16 | 0.0 | 3.5 | 0.0 | 4-8° C. | 6.45 | 259 | 2 |
| 16 | 0.0 | 35.0 | 1.0 | 4-8° C. | 6.11 | 300 | none |
| 16 | 4.4 | 3.5 | 1.0 | 4-8° C. | 6.37 | 266 | 2 |
| 16 | 4.4 | 35.0 | 0.0 | 4-8° C. | 6.01 | 316 | none |
| 7.0 | 0.0 | 3.5 | 0.0 | 4-8° C. | 6.55 | 242 | none |
| 7.0 | 0.0 | 35.0 | 1.0 | 4-8° C. | 6.19 | 296 | none |
| 7.0 | 4.4 | 3.5 | 1.0 | 4-8° C. | 7.04 | 253 | 2 |
| 7.0 | 4.4 | 35.0 | 0.0 | 4-8° C. | 6.84 | 315 | none |
| 16 | 0.0 | 3.5 | 1.0 | 4-8° C. | 6.01 | 260 | 2 |
| 16 | 0.0 | 35.0 | 0.0 | 4-8° C. | 6.01 | 304 | none |
| 16 | 4.4 | 3.5 | 0.0 | 4-8° C. | 6.48 | 269 | 2 |
| 16 | 4.4 | 35.0 | 1.0 | 4-8° C. | 6.01 | 310 | none |

Figure 2A:
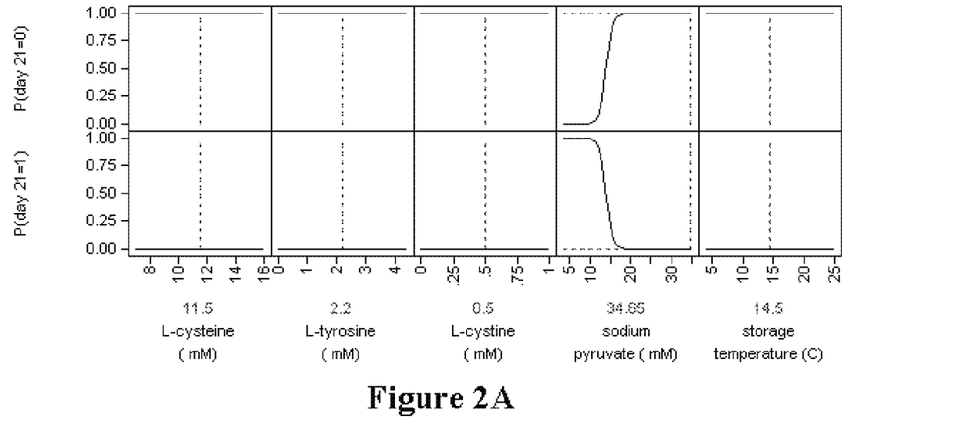
Figure 2B:
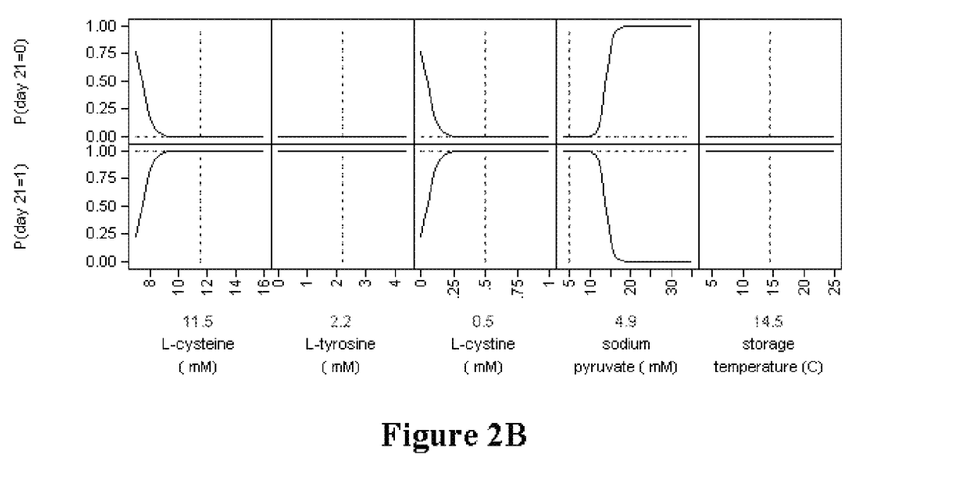
FIG. 2B: This figure is the same as FIG. 2A except that sodium pyruvate is set at 4.9 mM in all columns except that labeled "sodium pyruvate."

Data were entered into the software JMP® (SAS Institute Inc., Cary, N.C.), which produced FIGS. 2A and 2B. FIGS. 2A and 2B and Table 4 make a number of trends in the data obvious. First, media were approximately equally stable at room temperature or at refrigerator temperature, i.e., 4-8° C. The presence or absence of tyrosine within the tested range, that is, either 0.0 mM or 4.4 mM, had little or no effect on medium stability. However, higher concentrations of cysteine, cystine, or a combination of the two led to precipitation of media at low (3.5 mM), but not at high (35 mM), concentrations of sodium pyruvate. Thus, the addition of higher concentrations of sodium pyruvate can stabilize media containing the higher concentrations of cysteine and/or cystine tested in this experiment.

Example 5

Stabilizing Effects of Pyruvate on Feed Medium A

Using the Design of Experiment (DOE) portion of JMP® software (SAS Institute Inc., Cary, N.C.), an experiment was designed to measure the stability of Medium A (described above in Example 1) with varying amounts of added cystine, cysteine, tyrosine, and sodium pyruvate. The experiment tested the effects of (1) 0.0 and 1.12 mM cystine, (2) 0.0, 3.83, and 4.59 mM tyrosine, (3) 0.0, 6.83, and 12.53 mM cysteine, (4) 4.54, 9.09, 18.18, and 36.35 mM sodium pyruvate, and (5) all possible combinations thereof on medium stability. The media was compounded at room temperature, and its stability was assessed at 4-8° C. at days 0, 2, 4, 6, 9, 12, 14, 16, 19, and 21 days. Stability is recorded in Table 6, below, as explained in Example 3. Samples marked "none" had no precipitate on day 21, when the experiment was concluded.

TABLE 6

Stability of Feed Medium A with various additives

| Cystine (mM) | Tyrosine (mM) | Cysteine (mM) | Sodium pyruvate (mM) | pH | Osmo (mOsm) | Day on which precipitate was first noted |
|---|---|---|---|---|---|---|
| 0 | 0 | 0 | 4.54 | 6.99 | 299 | none |
| 1.12 | 0 | 0 | 4.54 | 6.97 | 287 | none |
| 0 | 3.83 | 0 | 4.54 | 7.01 | 296 | none |
| 1.12 | 3.83 | 0 | 4.54 | 6.99 | 300 | none |
| 0 | 4.59 | 0 | 4.54 | 6.98 | 283 | 2 |
| 1.12 | 4.59 | 0 | 4.54 | 7.00 | 300 | 2 |
| 0 | 0 | 6.83 | 4.54 | 6.97 | 300 | none |
| 1.12 | 0 | 6.83 | 4.54 | 6.97 | 293 | 4 |
| 0 | 3.83 | 6.83 | 4.54 | 7.01 | 288 | none |
| 1.12 | 3.83 | 6.83 | 4.54 | 7.00 | 294 | 2 |
| 0 | 4.59 | 6.83 | 4.54 | 6.99 | 297 | 2 |
| 1.12 | 4.59 | 6.83 | 4.54 | 6.99 | 300 | 2 |
| 0 | 0 | 12.53 | 4.54 | 6.95 | 292 | 6 |
| 1.12 | 0 | 12.53 | 4.54 | 6.94 | 288 | 2 |
| 0 | 3.83 | 12.53 | 4.54 | 7.05 | 300 | 4 |
| 1.12 | 3.83 | 12.53 | 4.54 | 6.92 | 291 | 2 |
| 0 | 4.59 | 12.53 | 4.54 | 6.94 | 305 | 2 |
| 1.12 | 4.59 | 12.53 | 4.54 | 6.94 | 302 | 2 |
| 0 | 0 | 0 | 9.09 | 6.99 | 299 | none |
| 1.12 | 0 | 0 | 9.09 | 6.93 | 293 | none |
| 0 | 3.83 | 0 | 9.09 | 7.01 | 309 | none |
| 1.12 | 3.83 | 0 | 9.09 | 6.99 | 304 | none |
| 0 | 4.59 | 0 | 9.09 | 6.94 | 303 | 4 |
| 1.12 | 4.59 | 0 | 9.09 | 6.99 | 308 | 2 |
| 0 | 0 | 6.83 | 9.09 | 7.02 | 303 | none |
| 1.12 | 0 | 6.83 | 9.09 | 7.01 | 293 | 4 |
| 0 | 3.83 | 6.83 | 9.09 | 6.89 | 294 | none |
| 1.12 | 3.83 | 6.83 | 9.09 | 6.98 | 302 | 2 |
| 0 | 4.59 | 6.83 | 9.09 | 6.95 | 302 | 2 |
| 1.12 | 4.59 | 6.83 | 9.09 | 7.01 | 306 | 2 |
| 0 | 0 | 12.53 | 9.09 | 6.97 | 300 | 21 |
| 1.12 | 0 | 12.53 | 9.09 | 6.99 | 299 | 2 |
| 0 | 3.83 | 12.53 | 9.09 | 6.99 | 303 | 6 |
| 1.12 | 3.83 | 12.53 | 9.09 | 7.01 | 307 | 2 |
| 0 | 4.59 | 12.53 | 9.09 | 6.99 | 310 | 2 |
| 1.12 | 4.59 | 12.53 | 9.09 | 7.00 | 311 | 2 |
| 0 | 0 | 0 | 18.18 | 6.97 | 312 | none |
| 1.12 | 0 | 0 | 18.18 | 7.02 | 310 | none |
| 0 | 3.83 | 0 | 18.18 | 6.99 | 312 | none |
| 1.12 | 3.83 | 0 | 18.18 | 6.98 | 317 | none |
| 0 | 4.59 | 0 | 18.18 | 7.02 | 303 | 2 |
| 1.12 | 4.59 | 0 | 18.18 | 7.03 | 316 | 2 |
| 0 | 0 | 6.83 | 18.18 | 6.97 | 296 | none |
| 1.12 | 0 | 6.83 | 18.18 | 7.02 | 303 | 6 |
| 0 | 3.83 | 6.83 | 18.18 | 7.03 | 316 | none |
| 1.12 | 3.83 | 6.83 | 18.18 | 6.98 | 310 | 4 |
| 0 | 4.59 | 6.83 | 18.18 | 6.98 | 309 | 4 |
| 1.12 | 4.59 | 6.83 | 18.18 | 7.05 | 313 | 2 |
| 0 | 0 | 12.53 | 18.18 | 6.98 | 315 | none |
| 1.12 | 0 | 12.53 | 18.18 | 6.97 | 307 | 6 |
| 0 | 3.83 | 12.53 | 18.18 | 6.97 | 312 | 21 |
| 1.12 | 3.83 | 12.53 | 18.18 | 7.01 | 315 | 4 |
| 0 | 4.59 | 12.53 | 18.18 | 7.00 | 320 | 2 |
| 1.12 | 4.59 | 12.53 | 18.18 | 7.02 | 318 | 2 |
| 0 | 0 | 0 | 36.35 | 6.97 | 330 | none |
| 1.12 | 0 | 0 | 36.35 | 6.97 | 342 | none |
| 0 | 3.83 | 0 | 36.35 | 7.00 | 348 | none |
| 1.12 | 3.83 | 0 | 36.35 | 6.98 | 347 | none |
| 0 | 4.59 | 0 | 36.35 | 6.98 | 343 | 6 |
| 1.12 | 4.59 | 0 | 36.35 | 7.00 | 346 | 4 |
| 0 | 0 | 6.83 | 36.35 | 7.04 | 331 | none |
| 1.12 | 0 | 6.83 | 36.35 | 7.01 | 357 | none |
| 0 | 3.83 | 6.83 | 36.35 | 6.97 | 349 | none |
| 1.12 | 3.83 | 6.83 | 36.35 | 7.02 | 351 | none |
| 0 | 4.59 | 6.83 | 36.35 | 7.05 | 349 | 4 |
| 1.12 | 4.59 | 6.83 | 36.35 | 7.02 | 360 | 4 |
| 0 | 0 | 12.53 | 36.35 | 6.98 | 315 | none |
| 1.12 | 0 | 12.53 | 36.35 | 6.94 | 344 | none |
| 0 | 3.83 | 12.53 | 36.35 | 6.99 | 350 | none |
| 1.12 | 3.83 | 12.53 | 36.35 | 7.00 | 348 | none |
| 0 | 4.59 | 12.53 | 36.35 | 6.98 | 357 | 4 |
| 1.12 | 4.59 | 12.53 | 36.35 | 6.99 | 354 | 4 |

Figure 3A:
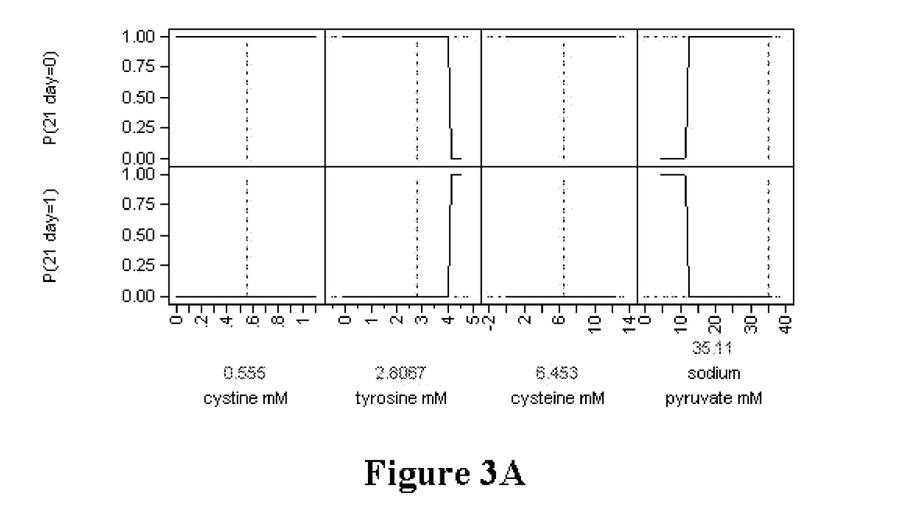
Figure 3B:
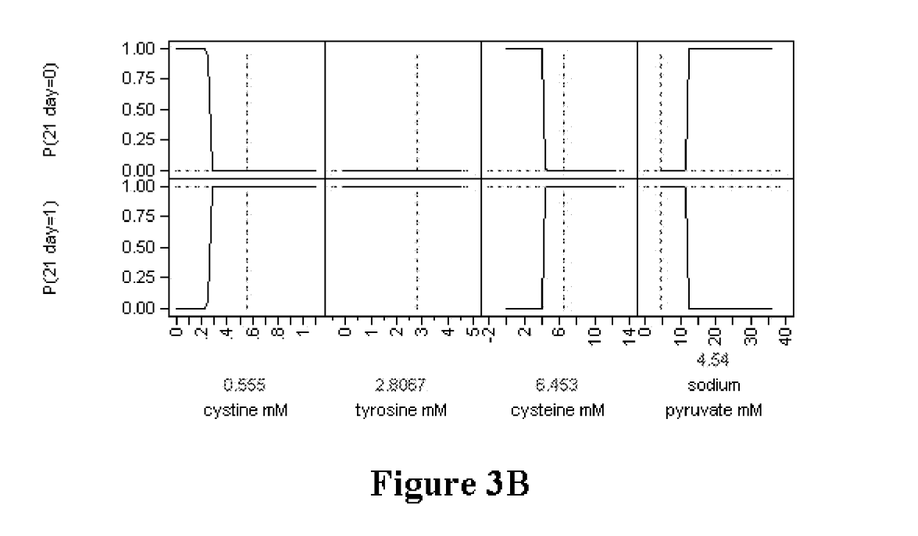
FIG. 3B: This figure is like FIG. 3A except sodium pyruvate is set at a concentration of 4.54 mM in all columns other than the rightmost column in which the concentration of sodium pyruvate varies.

FIGS. 3A and 3B and Table 6 highlight some aspects of the data. First, high levels of cystine, cysteine, or tyrosine increased precipitation. However, addition of the highest concentration of sodium pyruvate tested (36.36 mM) inhibited precipitation associated with cystine or cysteine and most of the concentrations of tyrosine tested, whereas lower concentrations of pyruvate tested were not as effective in stabilizing media. Addition of 9.09 or 18.18 mM pyruvate stabilized some samples as compared to samples containing 4.53 mM pyruvate. However, even 36.35 mM sodium pyruvate did not stabilize media containing 4.59 mM tyrosine.

What is claimed is:

1. A method for stabilizing a concentrated feed medium for feeding a mammalian cell culture comprising adding pyruvate to the feed medium,
    wherein the concentration of pyruvate after addition is at least 10 mM and not more than 100 mM,
    wherein the feed medium comprises cysteine at a concentration from 7 mM to 30 mM,
    wherein the feed medium comprises tyrosine at a concentration that is at least 1 mM and less than or equal to 4.6 mM, wherein the feed medium further comprises tryptophan at a concentration of 0.2-11 mM, histidine at a concentration of 0.6-67 mM, methionine at a concentration from 0.6-31 mM, phenylalanine at a concentration of 0.7-46 mM, isoleucine at a concentration of 1.6-80 mM, proline at a concentration of 2.6-130 mM, valine at a concentration of 2.5-128 mM, threonine at a concentration of 2.5-126 mM, serine at a concentration of 1.1-143 mM, lysine at a concentration of 2.4-165 mM, and leucine at a concentration of 2.2-115 mM, wherein cystine is not added to the feed medium at a concentration of more than 1.0 mM, wherein the pH of the feed medium is from 5.8 to about 7.4, and wherein the feed medium with the added pyruvate is stable for at least 1 week at 4-8° C.

2. The method of claim 1, wherein the feed medium comprises not more than 25 mM cysteine.

3. The method of claim 2, wherein the feed medium comprises at least 20 mM cysteine.

4. The method of claim 2, wherein the feed medium comprises not more than 20 mM cysteine.

5. The method of claim 1, wherein the feed medium comprises at least 4.0 mM tyrosine.

6. The method of claim 5, wherein the feed medium comprises about 4.6 mM tyrosine.

7. The method of claim 1, wherein the pH of the feed medium is from 6.0 to 7.2.

8. The method of claim 1, wherein the feed medium is serum free.

9. The method of claim 1, wherein the feed medium comprises a protein hydrolysate.

10. The method of claim 1, wherein no cystine is added to the feed medium.

11. The method of claim 1, wherein the mammalian cell culture is a CHO cell culture.

12. The method of claim 3,
wherein the feed medium comprises at least 4.0 mM tyrosine,
wherein no cystine is added to the feed medium, and
wherein the concentration of pyruvate after addition is at least 20 mM.

13. The method of claim 12, wherein the concentration of pyruvate after addition is at least 30 mM.

14. A feed medium for a mammalian cell culture comprising:
pyruvate at a concentration of at least 10 mM and not more than 100 mM,
cysteine at a concentration of at least 7 mM and not more than 40 mM,
tyrosine at a concentration that is at least 1 mM and less than or equal to 4.6 mM,
tryptophan at a concentration of 0.2-11 mM, histidine at a concentration of 0.6-67 mM, methionine at a concentration from 0.6-31 mM, phenylalanine at a concentration of 0.7-46 mM, isoleucine at a concentration of 1.6-80 mM, proline at a concentration of 2.6-130 mM, valine at a concentration of 2.5-128 mM, threonine at a concentration of 2.5-126 mM, serine at a concentration of 1.1-143 mM, lysine at a concentration of 2.4-165 mM, and leucine at a concentration of 2.2-115 mM,
wherein not more than 1.0 mM cystine is added to the medium,
wherein the pH of the feed medium is from 5.8 to 7.4, and
wherein the medium is stable for at least 1 week at 4-8° C.

15. The feed medium of claim 14, wherein the pH of the feed medium is from 6.0 to 7.2.

16. The feed medium of claim 14, wherein at least 20 mM pyruvate is added to the medium.

17. The feed medium of claim 16, wherein at least 30 mM pyruvate is added to the medium.

18. The feed medium of claim 14, wherein about 18, 20, 21, 22, 23, 24, 25, 26, 27, 28, 29, 30, 31, 32, 33, 34, 35, or 36 mM pyruvate is added to the medium.

19. The feed medium of claim 14, wherein at least 20 mM and not more than 25 mM cysteine is added to the medium.

20. The feed medium of claim 14, wherein at least 3 mM tyrosine is added to the medium.

21. The feed medium of claim 20, wherein at least 4 mM tyrosine is added to the medium.

22. The feed medium of claim 21, wherein about 4.6 mM tyrosine is added to the medium.

23. The feed medium of claim 14, wherein the feed medium is serum free.

24. The feed medium of claim 14, wherein a protein hydrolysate is added to the medium.

25. The feed medium of claim 14, wherein the feed medium is chemically defined.

26. The feed medium of claim 14, wherein the mammalian cell culture is a CHO cell culture, and wherein the pyruvate is sodium pyruvate.

27. The feed medium of claim 14, wherein cystine is not added to the medium.

28. The feed medium of claim 27,
wherein at least 4 mM tyrosine and at least 20 mM cysteine are added to the feed medium, and
wherein the pH of the feed medium is from 6.0 to 7.4.

29. The feed medium of claim 28, wherein at least 30 mM pyruvate is added to the feed medium.

30. The feed medium of claim 29, wherein at least 40 mM pyruvate is added to the feed medium.

31. The feed medium of claim 28, wherein about 4.6 mM tyrosine is added to the medium.

32. A feed medium comprising
from 25 mM to 45 mM pyruvate,
at least 7 mM cysteine and not more than 25 mM cysteine, and
tyrosine at a concentration that is at least 3.0 mM and less than or equal to 4.6 mM,
wherein the feed medium further comprises arginine at a concentration of 1-57 mM, tryptophan at a concentration of 0.2-11 mM, histidine at a concentration of 0.6-67 mM, methionine at a concentration from 0.6-31 mM, phenylalanine at a concentration of 0.7-46 mM, isoleucine at a concentration of 1.6-80 mM, proline at a concentration of 2.6-130 mM, valine at a concentration of 2.5-128 mM, threonine at a concentration of 2.5-126 mM, serine at a concentration of 1.1-143 mM, lysine at a concentration of 2.4-165 mM, and leucine at a concentration of 2.2-115 mM,
wherein not more than 1.0 mM cystine is added to the medium,
wherein the medium is stable for at least one week at 4-8° C.

33. A method for producing a protein comprising
culturing mammalian cells that produce the protein in a base medium,
feeding the culture with a feed medium, and
recovering the protein,
wherein the feed medium comprises pyruvate at a concentration of at least 10 mM and not more than 100 mM, cysteine at a concentration of at least 7 mM and not more than 40 mM, tyrosine at a concentration that is at least 1 mM and less than or equal to 4.6 mM, tryptophan at a concentration of 0.2-11 mM, histidine at a concentration of 0.6-67 mM, methionine at a concentration from 0.6-31 mM, phenylalanine at a concentration of 0.7-46 mM, isoleucine at a concentration of 1.6-80 mM, proline at a concentration of 2.6-130 mM, valine at a concentration of 2.5-128 mM, threonine at a concentration of 2.5-126 mM, serine at a concentration of 1.1-143 mM, lysine at a concentration of 2.4-165 mM, and leucine at a concentration of 2.2-115 mM, wherein not more than 1.0 mM cystine is added to the medium, wherein the pH of the feed medium is from 5.8 to 7.4, and wherein the medium is stable for at least 1 week at 4-8° C.

34. A method for producing a protein comprising culturing mammalian cells that produce the protein in a base medium, feeding the culture with a feed medium, and recovering the protein, wherein the feed medium comprises from 25 mM to 45 mM pyruvate, at least 7 mM cysteine and not more than 25 mM cysteine, tyrosine at a concentration of at least 3.0 mM and less than or equal to 4.6 mM, arginine at a concentration of 1-57 mM, tryptophan at a concentration of 0.2-11 mM, histidine at a concentration of 0.6-67 mM, methionine at a concentration from 0.6-31 mM, phenylalanine at a concentration of 0.7-46 mM, isoleucine at a concentration of 1.6-80 mM, proline at a concentration of 2.6-130 mM, valine at a concentration of 2.5-128 mM, threonine at a concentration of 2.5-126 mM, serine at a concentration of 1.1-143 mM, lysine at a concentration of 2.4-165 mM, and leucine at a concentration of 2.2-115 mM, wherein not more than 1.0 mM cystine is added to the medium, and wherein the medium is stable for at least one week at 4-8° C.

* * * * *